US012364546B2

(12) United States Patent
Atarot et al.

(10) Patent No.: US 12,364,546 B2
(45) Date of Patent: Jul. 22, 2025

(54) DEVICE AND METHOD FOR ASSISTING LAPAROSCOPIC SURGERY UTILIZING A TOUCH SCREEN

(71) Applicant: Asensus Surgical Europe S.a.r.l, Lugano (CH)

(72) Inventors: Gal Atarot, Kfar Saba (IL); Tal Nir, Haifa (IL); Motti Frimer, Zichron Yaakov (IL); Tami Harel, Haifa (IL)

(73) Assignee: Asensus Surgical Europe S.A.R.L., Lugano (CH)

( * ) Notice: Subject to any disclaimer, the term of this patent is extended or adjusted under 35 U.S.C. 154(b) by 0 days.

(21) Appl. No.: 17/962,440

(22) Filed: Oct. 7, 2022

(65) Prior Publication Data

US 2023/0040952 A1    Feb. 9, 2023

Related U.S. Application Data

(63) Continuation of application No. 15/317,121, filed as application No. PCT/IL2015/050579 on Jun. 8, 2015, now abandoned.
(Continued)

(51) Int. Cl.
*A61B 34/20*    (2016.01)
*A61B 1/00*    (2006.01)
(Continued)

(52) U.S. Cl.
CPC .......... *A61B 34/20* (2016.02); *A61B 1/00045* (2013.01); *A61B 1/3132* (2013.01);
(Continued)

(58) Field of Classification Search
CPC ... A61B 34/20; A61B 1/00045; A61B 1/3132; A61B 17/00234; A61B 34/25;
(Continued)

(56) References Cited

U.S. PATENT DOCUMENTS

2009/0245600 A1\* 10/2009 Hoffman ................ A61B 34/30
348/240.99
2009/0248036 A1\* 10/2009 Hoffman ................ A61B 34/32
606/130
(Continued)

FOREIGN PATENT DOCUMENTS

WO    WO-2013027200 A2 \*  2/2013 ......... A61B 1/00006

*Primary Examiner* — Anh T Nguyen
*Assistant Examiner* — Shankar Raj Ghimire

(57) ABSTRACT

A surgical controlling system, comprising: at least one surgical tool configured to be inserted into a surgical environment of a human body; at least one location estimating means configured for real-time localization of the 3D spatial position of said at least one surgical tool at any given time t; at least one movement detection means communicable with a movement's database and with said location estimating means; a controller having a processing means communicable with a controller's database; said controller's database is in communication with said movement detection means; and at least one display configured to real time provide an image of at least a portion of said surgical environment; wherein said controller is configured to direct said surgical tool to said location via said instructions provided by said controller; further wherein said location is real time updated on said display as said at least one surgical tool is moved.

6 Claims, 23 Drawing Sheets

Related U.S. Application Data

(60) Provisional application No. 62/009,240, filed on Jun. 8, 2014.

(51) Int. Cl.
| | |
|---|---|
| *A61B 1/313* | (2006.01) |
| *A61B 17/00* | (2006.01) |
| *A61B 34/00* | (2016.01) |
| *A61B 90/00* | (2016.01) |
| *G05B 19/00* | (2006.01) |
| *G16H 20/40* | (2018.01) |
| *G16H 40/63* | (2018.01) |

(52) U.S. Cl.
CPC ........ *A61B 17/00234* (2013.01); *A61B 34/00* (2016.02); *A61B 34/25* (2016.02); *A61B 90/03* (2016.02); *A61B 90/361* (2016.02); *G05B 19/00* (2013.01); *G16H 20/40* (2018.01); *G16H 40/63* (2018.01); *A61B 2017/00057* (2013.01); *A61B 2017/00119* (2013.01); *A61B 2017/00199* (2013.01); *A61B 2017/00207* (2013.01); *A61B 2017/00216* (2013.01); *A61B 2017/00221* (2013.01); *A61B 2017/00225* (2013.01); *A61B 2034/2048* (2016.02); *A61B 2034/2055* (2016.02); *A61B 2034/2065* (2016.02); *A61B 2090/0805* (2016.02); *A61B 2090/373* (2016.02); *A61B 2562/0257* (2013.01)

(58) Field of Classification Search
CPC .................. A61B 90/03; A61B 90/361; A61B 2017/00119; A61B 2017/00199; A61B 2017/00207

See application file for complete search history.

(56) References Cited

U.S. PATENT DOCUMENTS

| | | | |
|---|---|---|---|
| 2011/0152882 A1* | 6/2011 | Wenderow | A61B 5/742 606/130 |
| 2012/0254747 A1* | 10/2012 | Bocirnea | G16H 30/40 345/620 |
| 2013/0290887 A1* | 10/2013 | Sun | G06F 3/0482 715/764 |
| 2014/0163359 A1* | 6/2014 | Sholev | A61B 1/00011 600/407 |
| 2014/0296628 A1* | 10/2014 | Kirma | A61B 1/0655 600/103 |
| 2015/0220215 A1* | 8/2015 | Choi | G06F 3/0481 715/800 |
| 2015/0374209 A1* | 12/2015 | Yamamura | H04N 23/66 348/65 |
| 2016/0175057 A1* | 6/2016 | Ibach | A61B 1/00066 600/103 |
| 2016/0331213 A1* | 11/2016 | Kim | A61B 1/00048 |
| 2016/0354166 A1* | 12/2016 | Popovic | A61B 1/000094 |
| 2018/0324352 A1* | 11/2018 | Furuhata | H04N 23/63 |

* cited by examiner

DEVICE AND METHOD FOR ASSISTING LAPAROSCOPIC SURGERY UTILIZING A TOUCH SCREEN

CROSS-REFERENCE TO RELATED APPLICATIONS

This application is a continuation of U.S. application Ser. No. 15/317,121, filed Dec. 8, 2016, which claims priority to U.S. National Phase filing under 35 U.S.C. 371 of International (PCT) Patent Application No. PCT/IL2015/050579, filed Jun. 8, 2015, which claims priority from U.S. Provisional Patent Application No. 62/009,240, filed Jun. 8, 2014, both of which are incorporated by reference in their entirety.

FIELD OF THE INVENTION

The present invention generally pertains to a system and method for directing a laparoscopic system by means of at least one of a touchscreen, body portion of the user movement and eye movement, sound being made by the user.

BACKGROUND OF THE INVENTION

In laparoscopic surgery, the surgeon performs the operation through small holes using long instruments and observing the internal anatomy with an endoscope camera.

Laparoscopic surgery is becoming increasingly popular with patients because the scars are smaller and their period of recovery is shorter. Laparoscopic surgery requires special training for the surgeon and the theatre nursing staff. The equipment is often expensive and is not available in all hospitals.

During laparoscopic surgery, it is often required to shift the spatial placement of the endoscope in order to present the surgeon with an optimal view. Conventional laparoscopic surgery makes use of either human assistants that manually shift the instrumentation or, alternatively, robotic automated assistants. Automated assistants utilize interfaces that enable the surgeon to direct the mechanical movement of the assistant, achieving a shift in the camera view.

Research has suggested that these systems divert the surgeon's focus from the major task at hand. Therefore, technologies assisted by magnets and image processing have been developed to simplify interfacing control. However, these improved technologies still fail to address another complicating interface aspect of laparoscopic surgery, in that the surgeon must still keep his attention on the process of moving until the movement is complete. If the surgeon uses a hand-operated control, his hand must remain on the control until the movement is complete. If the surgeon uses voice controls, he must continue to issue voice commands until the movement is complete. Only then can he return his attention (and his hand or hands) to the surgical procedure.

Hence, there is still a long felt need for a method of directing a laparoscopic system to a desired location that does not require the surgeon to focus on the process of moving the laparoscopic system.

SUMMARY OF THE INVENTION

It is an object of the present invention to disclose a system and method for directing a laparoscopic system by means of at least one of a touchscreen, body portion of the user movement, sound being made by the user eye movement.

It is another object of the present invention to disclose a surgical controlling system, comprising:

a. at least one surgical tool configured to be inserted into a surgical environment of a human body for assisting a surgical procedure;
b. at least one location estimating means configured for real-time localization of the 3D spatial position of said at least one surgical tool at any given time t;
c. at least one movement detection means communicable with a movement's database and with said location estimating means; said movement's database is configured to store said 3D spatial position of said at least one surgical tool at time $t_f$ and at time $t_0$; where $t_f > t_0$; said movement detection means is configured to detect movement of said at least one surgical tool if the 3D spatial position of said at least one surgical tool at time $t_f$ is different than said 3D spatial position of said at least one surgical tool at time $t_0$; and,
d. a controller having a processing means communicable with a controller's database, said controller configured to control the spatial position of said at least one surgical tool; said controller's database is in communication with said movement detection means; said controller configured to provide instructions for moving said at least one surgical tool; and
e. input receiving means configured to receive input of at least one location within said surgical environment of said human body; and
f. at least one display configured to real time provide an image of at least a portion of said surgical environment; wherein said controller is configured to direct said surgical tool to said location via said instructions provided by said controller;
further wherein said location is real time updated on said display as said at least one surgical tool is moved.

It is another object of the present invention to disclose the surgical controlling system, wherein said input receiving means is selected from a group consisting of: (a) a touchscreen in wired or wireless communication with said controller, configured to display an image of at least a portion of said surgical environment of said human body and to receive input of at least one location within said surgical environment of said human body; (b) at least one first camera, in wired or wireless communication with said controller, configured to detect movement of an eye; and, (c) at least one second camera, in wired or wireless communication with said controller, configured to detect movement of a hand; and any combination thereof.

It is another object of the present invention to disclose the surgical controlling system, wherein said portion of said touchscreen is that which displays the image of said location.

It is another object of the present invention to disclose the surgical controlling system, wherein said portion of said touchscreen displays a direction indicator, said direction indicator selected from a group consisting of: an arrow pointing in a predefined direction, a line pointing in a predefined direction, a pointer pointing in a predefined direction, the word "left", the word "right" the word "up", the word "down", the word "forward", the word "back", the word "zoom", the word "in", the word "out", and any combination thereof.

It is another object of the present invention to disclose the surgical controlling system, wherein said location within said surgical environment of said human body is determinable from at least one of a group consisting of pressure on a portion of said touchscreen, movement of said hand, and movement of said eye.

It is another object of the present invention to disclose the surgical controlling system, wherein said movement of said hand is selected from a group consisting of: direction of movement of said hand, speed of movement of said hand and any combination thereof.

It is another object of the present invention to disclose the surgical controlling system, wherein said direction of movement of said hand is selected from a group consisting of: left, right, up, down, forward, back, and any combination thereof.

It is another object of the present invention to disclose the surgical controlling system, wherein said movement of said eye is selected from a group consisting of: direction of movement of said eye, speed of movement of said eye, closing of said eye, and any combination thereof.

It is another object of the present invention to disclose the surgical controlling system, wherein said direction of movement of said eye is selected from a group consisting of: left, right, up, down, and any combination thereof.

It is another object of the present invention to disclose the surgical controlling system, wherein at least one of the following is being held true (a) said system additionally comprises an endoscope; said endoscope is configured to provide real-time image of said surgical environment; (b) at least one of said surgical tools is an endoscope configured to provide at least one real-time image of said surgical environment.

It is another object of the present invention to disclose the surgical controlling system, wherein said tool comprises at least one proximity sensor positioned on the outer circumference of the same.

It is another object of the present invention to disclose the surgical controlling system, wherein said instructions comprise a predetermined set of rules selected from a group consisting of: most used tool rule, right tool rule, left tool rule, field of view rule, no fly zone rule, a route rule, environmental rule, operator input rule, proximity rule; collision prevention rule, history-based rule, tool-dependent allowed and restricted movements rule, preferred volume zone rule, preferred tool rule, movement detection rule, tagged tool rule, change of speed rule and any combination thereof.

It is another object of the present invention to disclose the surgical controlling system, wherein said route rule comprises a communicable database storing predefined route in which said at least one surgical tool is configured to move within said surgical environment; said predefined route comprises n 3D spatial positions of said at least one surgical tool; n is an integer greater than or equal to 2; said allowed movements are movements in which said at least one surgical tool is located substantially in at least one of said n 3D spatial positions of said predefined route, and said restricted movements are movements in which said location of said at least one surgical tool is substantially different from said n 3D spatial positions of said predefined route.

It is another object of the present invention to disclose the surgical controlling system, wherein said environmental rule comprises a comprises a communicable database; said communicable database configured to receive at least one real-time image of said surgical environment and is configured to perform real-time image processing of the same and to determine the 3D spatial position of hazards or obstacles in said surgical environment; said environmental rule is configured to determine said allowed and restricted movements according to said hazards or obstacles in said surgical environment, such that said restricted movements are movements in which said at least one surgical tool is located substantially in at least one of said 3D spatial positions, and said allowed movements are movements in which the location of said at least one surgical tool is substantially different from said 3D spatial positions.

It is another object of the present invention to disclose the surgical controlling system, wherein said hazards or obstacles in said surgical environment are selected from a group consisting of tissue, a surgical tool, an organ, an endoscope and any combination thereof.

It is another object of the present invention to disclose the surgical controlling system, wherein said operator input rule comprises a communicable database; said communicable database is configured to receive an input from the operator of said system regarding said allowed and restricted movements of said at least one surgical tool.

It is another object of the present invention to disclose the surgical controlling system, wherein said input comprises n 3D spatial positions; n is an integer greater than or equal to 2; wherein at least one of which is defined as allowed location and at least one of which is defined as restricted location, such that said allowed movements are movements in which said at least one surgical tool is located substantially in at least one of said n 3D spatial positions, and said restricted movements are movements in which the location of said at least one surgical tool is substantially different from said n 3D spatial positions.

It is another object of the present invention to disclose the surgical controlling system, wherein said input comprises at least one rule according to which allowed and restricted movements of said at least one surgical tool are determined, such that the spatial position of said at least one surgical tool is controlled by said controller according to said allowed and restricted movements.

It is another object of the present invention to disclose the surgical controlling system, wherein said operator input rule converts an allowed movement to a restricted movement and a restricted movement to an allowed movement.

It is another object of the present invention to disclose the surgical controlling system, wherein said proximity rule is configured to define a predetermined distance between at least two surgical tools; said allowed movements are movements which are within the range or out of the range of said predetermined distance, and said restricted movements are movements which are out of the range or within the range of said predetermined distance.

It is another object of the present invention to disclose the surgical controlling system, wherein said proximity rule is configured to define a predetermined angle between at least three surgical tools; said allowed movements are movements which are within the range or out of the range of said predetermined angle, and said restricted movements are movements which are out of the range or within the range of said predetermined angle.

It is another object of the present invention to disclose the surgical controlling system, wherein said collision prevention rule is configured to define a predetermined distance between said at least one surgical tool and an anatomical element within said surgical environment; said allowed movements are movements which are in a range that is larger than said predetermined distance, and said restricted movements are movements which is in a range that is smaller than said predetermined distance.

It is another object of the present invention to disclose the surgical controlling system, wherein said anatomical element is selected from a group consisting of tissue, organ, another surgical tool and any combination thereof.

It is another object of the present invention to disclose the surgical controlling system, wherein said right tool rule is configured to determine said allowed movement of said endoscope according to the movement of the surgical tool positioned to right of said endoscope; further wherein said left tool rule is configured to determine said allowed movement of said endoscope according to the movement of the surgical tool positioned to left of said endoscope.

It is another object of the present invention to disclose the surgical controlling system, wherein said tagged tool rule comprises means configured to tag at least one surgical tool within said surgical environment and to determine said allowed movement of said endoscope to constantly track the movement of said tagged surgical tool.

It is another object of the present invention to disclose the surgical controlling system, wherein said field of view rule comprises a communicable database comprising n 3D spatial positions; n is an integer greater than or equal to 2; the combination of all of said n 3D spatial positions provides a predetermined field of view; said field of view rule is configured to determine said allowed movement of said endoscope within said n 3D spatial positions so as to maintain a constant field of view, such that said allowed movements are movements in which said endoscope is located substantially in at least one of said n 3D spatial positions, and said restricted movements are movements in which the location of said endoscope is substantially different from said n 3D spatial positions.

It is another object of the present invention to disclose the surgical controlling system, wherein said preferred volume zone rule comprises a communicable database comprising n 3D spatial positions; n is an integer greater than or equal to 2; said n 3D spatial positions provides said preferred volume zone; said preferred volume zone rule is configured to determine said allowed movement of said endoscope within said n 3D spatial positions and restricted movement of said endoscope outside said n 3D spatial positions, such that said allowed movements are movements in which said endoscope is located substantially in at least one of said n 3D spatial positions, and said restricted movements are movements in which the location of said endoscope is substantially different from said n 3D spatial positions.

It is another object of the present invention to disclose the surgical controlling system, wherein said preferred tool rule comprises a communicable database, said database stores a preferred tool; said preferred tool rule is configured to determine said allowed movement of said endoscope to constantly track the movement of said preferred tool.

It is another object of the present invention to disclose the surgical controlling system, wherein said no fly zone rule comprises a communicable database comprising n 3D spatial positions; n is an integer greater than or equal to 2; said n 3D spatial positions define a predetermined volume within said surgical environment; said no fly zone rule is configured to determine said restricted movement if said movement is within said no fly zone and allowed movement if said movement is outside said no fly zone, such that said restricted movements are movements in which said at least one of said surgical tool is located substantially in at least one of said n 3D spatial positions, and said allowed movements are movements in which the location of said at least one endoscope is substantially different from said n 3D spatial positions.

It is another object of the present invention to disclose the surgical controlling system, wherein said most used tool rule comprises a communicable database counting the amount of movement of each said surgical tool; said most used tool rule is configured to constantly position said endoscope to track the movement of the most moved surgical tool.

It is another object of the present invention to disclose the surgical controlling system, wherein said system further comprises a maneuvering subsystem communicable with said controller, said maneuvering subsystem is configured to spatially reposition said at least one surgical tool during a surgery according to said predetermined set of rules; further wherein said system is configured to alert the physician of said restricted movement of said at least one surgical tool.

It is another object of the present invention to disclose the surgical controlling system, wherein said alert is selected from a group consisting of audio signaling, voice signaling, light signaling, flashing signaling and any combination thereof.

It is another object of the present invention to disclose the surgical controlling system, wherein said allowed movement is permitted by said controller and said restricted movement is denied by said controller.

It is another object of the present invention to disclose the surgical controlling system, wherein said history-based rule comprises a communicable database storing each 3D spatial position of each said surgical tool, such that each movement of each surgical tool is stored; said history-based rule is configured to determine said allowed and restricted movements according to historical movements of said at least one surgical tool, such that said allowed movements are movements in which said at least one surgical tool is located substantially in at least one of said 3D spatial positions, and said restricted movements are movements in which the location of said at least one surgical tool is substantially different from said n 3D spatial positions.

It is another object of the present invention to disclose the surgical controlling system, wherein said tool-dependent allowed and restricted movements rule comprises a communicable database; said communicable database is configured to store predetermined characteristics of at least one of said surgical tool; said tool-dependent allowed and restricted movements rule is configured to determine said allowed and restricted movements according to said predetermined characteristics of said surgical tool; such that allowed movements are movements of said endoscope which track said surgical tool having said predetermined characteristics.

It is another object of the present invention to disclose the surgical controlling system, wherein said predetermined characteristics of said surgical tool are selected from a group consisting of: physical dimensions, structure, weight, sharpness, and any combination thereof.

It is another object of the present invention to disclose the surgical controlling system, wherein said movement detection rule comprises a communicable database comprising the real-time 3D spatial positions of each said surgical tool; said movement detection rule is configured to detect movement of said at least one surgical tool when a change in said 3D spatial positions is received, such that said allowed movements are movements in which said endoscope is re-directed to focus on said moving surgical tool.

It is another object of the present invention to disclose the surgical controlling system, further comprising a maneuvering subsystem communicable with said controller, said maneuvering subsystem is configured to spatially reposition said at least one surgical tool during a surgery according to said predetermined set of rules, such that if said movement of said at least one surgical tool is a restricted movement, said maneuvering subsystem prevents said movement.

It is another object of the present invention to disclose the surgical controlling system, wherein said at least one location estimating means comprises at least one endoscope configured to acquire real-time images of said surgical environment within said human body; and at least one surgical instrument spatial location software configured to receive said real-time images of said surgical environment and to estimate said 3D spatial position of said at least one surgical tool.

It is another object of the present invention to disclose the surgical controlling system, wherein said at least one location estimating means comprises (a) at least one element selected from a group consisting of optical imaging means, radio frequency transmitting and receiving means, at least one mark on said at least one surgical tool and any combination thereof; and, (b) at least one surgical instrument spatial location software configured to estimate said 3D spatial position of said at least one surgical tool by means of said element.

It is another object of the present invention to disclose the surgical controlling system, wherein said at least one location estimating means is an interface subsystem between a surgeon and said at least one surgical tool, the interface subsystem comprising:
  a. at least one array comprising N regular or pattern light sources, where N is a positive integer;
  b. at least one array comprising M cameras, each of the M cameras, where M is a positive integer;
  c. optional optical markers and means for attaching the optical marker to the at least one surgical tool; and;
  d. a computerized algorithm operable via the controller, the computerized algorithm configured to process images received by each camera of each of the M cameras and to calculate therefrom the position of each of the tools, and further configured to provide automatically the results of the calculation to the human operator of the interface.

It is another object of the present invention to disclose a method of using a surgical controlling system, comprising steps of:
  a. providing a surgical controlling system comprising:
    i. at least one surgical tool configured to be inserted into a surgical environment of a human body for assisting a surgical procedure;
    ii. at least one location estimating means configured for real-time localization of the 3D spatial position of said at least one surgical tool at any given time t;
    iii. at least one movement detection means communicable with a movement's database and with said location estimating means; said movement's database is configured to store said 3D spatial position of said at least one surgical tool at time $t_f$ and at time $t_0$; where $t_f > t_0$; said movement detection means is configured to detect movement of said at least one surgical tool if the 3D spatial position of said at least one surgical tool at time $t_f$ is different than said 3D spatial position of said at least one surgical tool at time $t_0$; and,
    iv. a controller having a processing means communicable with a controller's database, said controller configured to control the spatial position of said at least one surgical tool; said controller's database is in communication with said movement detection means; and
    v. input receiving means configured to receive input of at least one location within said surgical environment of said human body; and
    vi. at least one display configured to real time provide an image of at least a portion of said surgical environment;
  b. inserting at least one said surgical tool into said surgical environment;
  c. displaying said at least a portion of said surgical environment;
  d. receiving input of at least one location within said surgical environment of said human body;
  e. estimating the 3D spatial position of at least one said surgical tool; and
  f. directing and moving said surgical tool to said location via instructions provided by said controller
wherein said location is real time updated on said display as said at least one surgical tool is moved.

It is another object to disclose the method, additionally comprising steps of selecting said input receiving means from a group consisting of: (a) at least one touchscreen in wired or wireless communication with said controller, configured to display an image of at least a portion of said surgical environment of said human body and to receive input of at least one location within said surgical environment of said human body; (b) at least one first camera, in wired or wireless communication with said controller, configured to detect movement of an eye; and (c) at least one second camera, in wired or wireless communication with said controller, configured to detect movement of a hand, and any combination thereof.

It is another object to disclose the method, additionally comprising steps of receiving said input in a manner selected from a group consisting of: (a) providing said at least one touchscreen, displaying said image of at least a portion of said surgical environment via said touchscreen; and determining said location within said surgical environment of said human body from pressure on a portion of said touchscreen; (b) providing said at least one first camera and determining said movement of said eye; and (c) providing said at least one second camera and determining said movement of said hand.

It is another object of the present invention to disclose the method, additionally comprising steps of selecting said portion of said touchscreen to be that which displays the image of said location.

It is another object of the present invention to disclose the method, additionally comprising steps of displaying a direction indicator on said portion of said touchscreen, said direction indicator selected from a group consisting of: an arrow pointing in a predefined direction, a line pointing in a predefined direction, a pointer pointing in a predefined direction, the word "left", the word "right" the word "up", the word "down", the word "forward", the word "back", the word "zoom", the word "in", the word "out", and any combination thereof.

It is another object of the present invention to disclose the method, additionally comprising steps of determining, for said movement of said hand, at least one of a group consisting of: direction of movement of said hand and speed of movement of said hand.

It is another object of the present invention to disclose the method, additionally comprising steps of selecting said direction of movement of said hand from a group consisting of: left, right, up, down, forward, back, and any combination thereof.

It is another object of the present invention to disclose the method, additionally comprising steps of determining, for said movement of said eye, at least one of a group consisting of: direction of movement of said eye, speed of movement of said eye, closing of said eye.

It is another object of the present invention to disclose the method, additionally comprising steps of selecting said direction of movement of said eye from a group consisting of: left, right, up, down, and any combination thereof.

It is another object of the present invention to disclose the method, additionally comprising at least one of the following steps: (a) additionally providing an endoscope for said system; and providing at least one real-time image of said surgical environment by means of said endoscope; (b) selecting at least one of said surgical tools to be an endoscope and providing at least one real-time image of said surgical environment by means of said endoscope.

It is another object to disclose the method, additionally comprising step of positioning at least one proximity sensor on the outer circumference of said tool.

It is another object to disclose the method, additionally comprising step of selecting said instructions from a predetermined set of rules selected from a group consisting of: most used tool rule, right tool rule, left tool rule, field of view rule, no fly zone rule, a route rule, environmental rule, operator input rule, proximity rule; collision prevention rule, history-based rule, tool-dependent allowed and restricted movements rule, preferred volume zone rule, preferred tool rule, movement detection rule, tagged tool rule, change of speed rule and any combination thereof.

It is another object to disclose the method, wherein said route rule comprises steps of: providing a communicable database; storing a predefined route in which said at least one surgical tool is configured to move within said surgical environment; comprising said predefined route of n 3D spatial positions of said at least one surgical tool, n is an integer greater than or equal to 2; said allowed movements are movements in which said at least one surgical tool is located substantially in at least one of said n 3D spatial positions of said predefined route, and said restricted movements are movements in which said location of said at least one surgical tool is substantially different from said n 3D spatial positions of said predefined route.

It is another object to disclose the method, wherein said environmental rule comprises steps of: providing a communicable database; receiving at least one real-time image of said surgical environment in said communicable database; performing real-time image processing of the same and determining the 3D spatial position of hazards or obstacles in said surgical environment; determining said allowed and restricted movements according to said hazards or obstacles in said surgical environment, such that said restricted movements are movements in which said at least one surgical tool is located substantially in at least one of said 3D spatial positions, and said allowed movements are movements in which the location of said at least one surgical tool is substantially different from said 3D spatial positions.

It is another object to disclose the method, additionally comprising step of selecting said hazards or obstacles in said surgical environment from a group consisting of: tissue, a surgical tool, an organ, an endoscope and any combination thereof.

It is another object to disclose the method, wherein said operator input rule comprises steps of: providing a communicable database; and receiving input from an operator of said system regarding said allowed and restricted movements of said at least one surgical tool.

It is another object to disclose the method, additionally comprising steps of: comprising said input of n 3D spatial positions, n is an integer greater than or equal to 2; defining at least one of said spatial positions as an allowed location; defining at least one of said spatial positions as a restricted location; such that said allowed movements are movements in which said at least one surgical tool is located substantially in at least one of said n 3D spatial positions, and said restricted movements are movements in which the location of said at least one surgical tool is substantially different from said n 3D spatial positions.

It is another object to disclose the method, additionally comprising steps of: determining allowed and restricted movements of said at least one surgical tool from said input by means of at least one rule and, controlling such the spatial position of said at least one surgical tool by said controller according to said allowed and restricted movements.

It is another object to disclose the method, wherein said operator input rule comprises steps of: converting an allowed movement to a restricted movement and converting a restricted movement to an allowed movement.

It is another object to disclose the method, wherein said proximity rule comprises step of: defining a predetermined distance between at least two surgical tools; said allowed movements are movements which are within the range or out of the range of said predetermined distance, and said restricted movements are movements which are out of the range or within the range of said predetermined distance.

It is another object to disclose the method, wherein said proximity rule comprises step of: defining a predetermined angle between at least three surgical tools; said allowed movements are movements which are within the range or out of the range of said predetermined angle, and said restricted movements are movements which are out of the range or within the range of said predetermined angle.

It is another object to disclose the method, wherein said collision prevention rule comprises step of: defining a predetermined distance between said at least one surgical tool and an anatomical element within said surgical environment; said allowed movements are movements which are in a range that is larger than said predetermined distance, and said restricted movements are movements which is in a range that is smaller than said predetermined distance.

It is another object to disclose the method, additionally comprising step of selecting said anatomical element from a group consisting of tissue, organ, another surgical tool and any combination thereof.

It is another object to disclose the method, wherein said right tool rule comprises step of determining said allowed movement of said endoscope according to the movement of the surgical tool positioned to right of said endoscope; further wherein said left tool rule comprises step of determining said allowed movement of said endoscope according to the movement of the surgical tool positioned to left of said endoscope.

It is another object to disclose the method, wherein said tagged tool rule comprises steps of: tagging at least one surgical tool within said surgical environment and determining said allowed movements of said endoscope to be movements that constantly track the movement of said tagged surgical tool.

It is another object to disclose the method, wherein said field of view rule comprises steps of: providing a communicable database comprising n 3D spatial positions; n is an integer greater than or equal to 2; generating a field of view from the combination of all of said n 3D spatial positions; maintaining a constant field of view by determining said allowed movement of said endoscope to be within said n 3D spatial positions, such that said allowed movements are movements in which said endoscope is located substantially in at least one of said n 3D spatial positions, and said restricted movements are movements in which the location of said endoscope is substantially different from said n 3D spatial positions.

It is another object to disclose the method, wherein said preferred volume zone rule comprises steps of: providing a communicable database comprising n 3D spatial positions; n is an integer greater than or equal to 2; generating said preferred volume zone from said n 3D spatial positions; determining said allowed movement of said endoscope to be within said n 3D spatial positions and said restricted movement of said endoscope to be outside said n 3D spatial positions, such that said allowed movements are movements in which said endoscope is located substantially in at least one of said n 3D spatial positions, and said restricted movements are movements in which the location of said endoscope is substantially different from said n 3D spatial positions.

It is another object to disclose the method, wherein said preferred tool rule comprises steps of: providing a communicable database, storing a preferred tool in said database; and determining said allowed movement of said endoscope so as to constantly track the movement of said preferred tool.

It is another object to disclose the method, wherein said no fly zone rule comprises steps of: providing a communicable database comprising n 3D spatial positions, n is an integer greater than or equal to 2; defining a predetermined volume within said surgical environment from said n 3D spatial positions; determining said restricted movement to be said movement within said no fly zone; determining said allowed movement to be said movement outside said no fly zone, such that said restricted movements are movements in which said at least one of said surgical tool is located substantially in at least one of said n 3D spatial positions, and said allowed movements are movements in which the location of said at least one endoscope is substantially different from said n 3D spatial positions.

It is another object to disclose the method, wherein said most used tool rule comprises steps of: providing a communicable database; counting the amount of movement of each said surgical tool; constantly positioning said endoscope to track movement of the most moved surgical tool.

It is another object to disclose the method, additionally comprising steps of providing a maneuvering subsystem communicable with said controller, spatially repositioning said at least one surgical tool during a surgery according to said predetermined set of rules; and alerting the physician of said restricted movement of said at least one surgical tool.

It is another object to disclose the method, additionally comprising steps of selecting said alert from a group consisting of: audio signaling, voice signaling, light signaling, flashing signaling and any combination thereof.

It is another object to disclose the method, additionally comprising steps of defining said allowed movement as a movement permitted by said controller and defining said restricted movement as a movement denied by said controller.

It is another object to disclose the method, wherein said history-based rule comprises steps of: providing a communicable database storing each 3D spatial position of each said surgical tool, such that each movement of each surgical tool is stored; determining said allowed and restricted movements according to historical movements of said at least one surgical tool, such that said allowed movements are movements in which said at least one surgical tool is located substantially in at least one of said 3D spatial positions, and said restricted movements are movements in which the location of said at least one surgical tool is substantially different from said n 3D spatial positions.

It is another object to disclose the method, wherein said tool-dependent allowed and restricted movements rule comprises steps of: providing a communicable database; storing predetermined characteristics of at least one said surgical tool; determining said allowed and restricted movements according to said predetermined characteristics of said surgical tool; such that allowed movements are movements of said endoscope which track said surgical tool having said predetermined characteristics.

It is another object to disclose the method, additionally comprising step of selecting said predetermined characteristics of said surgical tool from a group consisting of: physical dimensions, structure, weight, sharpness, and any combination thereof.

It is another object to disclose the method, wherein said movement detection rule comprises steps of: providing a communicable database comprising the real-time 3D spatial positions of each said surgical tool; detecting movement of said at least one surgical tool when a change in said 3D spatial positions is received, such that said allowed movements are movements in which said endoscope is re-directed to focus on said moving surgical tool.

It is another object to disclose the method, additionally comprising steps of providing a maneuvering subsystem communicable with said controller, spatially repositioning said at least one surgical tool during a surgery according to said predetermined set of rules, such that if said movement of said at least one surgical tool is a restricted movement, said maneuvering subsystem prevents said movement.

It is another object to disclose the method, additionally comprising steps of comprising said at least one location estimating means of at least one endoscope configured to acquire real-time images of said surgical environment within said human body; providing at least one surgical instrument spatial location software; receiving said real-time images of said surgical environment from said endoscope and estimating said 3D spatial position of said at least one surgical tool using said spatial location software.

It is another object to disclose the method, additionally comprising step of providing said at least one location estimating means comprising (a) at least one element selected from a group consisting of optical imaging means, radio frequency transmitting and receiving means, at least one mark on said at least one surgical tool and any combination thereof; and, (b) at least one surgical instrument spatial location software configured to estimate said 3D spatial position of said at least one surgical tool by means of said element.

It is another object to disclose the method, additionally comprising step of selecting said at least one location estimating means to be an interface subsystem between a surgeon and said at least one surgical tool, the interface subsystem comprising:
  a. at least one array comprising N regular or pattern light sources, where N is a positive integer;
  b. at least one array comprising M cameras, each of the M cameras, where M is a positive integer;
  c. optional optical markers and means for attaching the optical marker to the at least one surgical tool; and;
  d. a computerized algorithm operable via the controller, the computerized algorithm configured to process images received by each camera of each of the M cameras and to calculate therefrom the position of each of the tools, and further configured to provide automatically the results of the calculation to the human operator of the interface.

It is another object of the present invention to disclose a surgical controlling system, comprising:

a. at least one surgical tool configured to be inserted into a surgical environment of a human body for assisting a surgical procedure;
b. at least one location estimating means configured for real-time localization of the 3D spatial position of said at least one surgical tool at any given time t;
c. at least one movement detection means communicable with a movement's database and with said location estimating means; said movement's database is configured to store said 3D spatial position of said at least one surgical tool at time $t_f$ and at time $t_0$; where $t_f > t_0$; said movement detection means is configured to detect movement of said at least one surgical tool if the 3D spatial position of said at least one surgical tool at time $t_f$ is different than said 3D spatial position of said at least one surgical tool at time $t_0$; and,
d. a controller having a processing means communicable with a controller's database, said controller configured to control the spatial position of said at least one surgical tool; said controller's database is in communication with said movement detection means; said controller configured to provide instructions for moving said at least one surgical tool; and
e. input receiving means configured to receive input of at least one location within said surgical environment of said human body; and
f. at least one display configured to real time provide an image of at least a portion of said surgical environment;
wherein said controller is configured to direct said surgical tool to said location via said instructions provided by said controller;
wherein said location is real time updated on said display as said at least one surgical tool is moved
further wherein said input receiving means is a touchscreen in wired or wireless communication with said controller, configured to display an image of at least a portion of said surgical environment of said human body and to receive input of at least one location within said surgical environment of said human body.

It is another object of the present invention to disclose the surgical controlling system, wherein said portion of said touchscreen is that which displays the image of said location.

It is another object of the present invention to disclose the surgical controlling system, wherein said portion of said touchscreen displays a direction indicator, said direction indicator selected from a group consisting of: an arrow pointing in a predefined direction, a line pointing in a predefined direction, a pointer pointing in a predefined direction, the word "left", the word "right" the word "up", the word "down", the word "forward", the word "back", the word "zoom", the word "in", the word "out", and any combination thereof.

It is another object to disclose the surgical controlling system, wherein said location within said surgical environment of said human body is determinable from pressure on a portion of said touchscreen.

It is another object to disclose the surgical controlling system, wherein said portion of said touchscreen is that which displays the image of said location.

It is another object to disclose the surgical controlling system, wherein said portion of said touchscreen displays a direction indicator, said direction indicator selected from a group consisting of: an arrow pointing in a predefined direction, a line pointing in a predefined direction, a pointer pointing in a predefined direction, the word "left", the word "right" the word "up", the word "down", the word "for-ward", the word "back", the word "zoom", the word "in", the word "out", and any combination thereof.

It is another object of the present invention to disclose the surgical controlling system, wherein said input receiving means is additionally selected from a group consisting of: (a) at least one first camera, in wired or wireless communication with said controller, configured to detect movement of an eye; and, (h) at least one second camera, in wired or wireless communication with said controller, configured to detect movement of a hand; and any combination thereof.

It is another object of the present invention to disclose the surgical controlling system, wherein said location within said surgical environment of said human body is determinable from at least one of a group consisting of: movement of said hand, and movement of said eye.

It is another object of the present invention to disclose the surgical controlling system, wherein said movement of said hand is selected from a group consisting of: direction of movement of said hand, speed of movement of said hand and any combination thereof.

It is another object of the present invention to disclose the surgical controlling system, wherein said direction of movement of said hand is selected from a group consisting of: left, right, up, down, forward, back, and any combination thereof.

It is another object of the present invention to disclose the surgical controlling system, wherein said movement of said eye is selected from a group consisting of: direction of movement of said eye, speed of movement of said eye, closing of said eye, and any combination thereof.

It is another object of the present invention to disclose the surgical controlling system, wherein said direction of movement of said eye is selected from a group consisting of: left, right, up, down, and any combination thereof.

It is another object of the present invention to disclose the surgical controlling system, wherein at least one of the following is being held true (a) said system additionally comprises an endoscope; said endoscope is configured to provide real-time image of said surgical environment; (b) at least one of said surgical tools is an endoscope configured to provide at least one real-time image of said surgical environment.

It is another object of the present invention to disclose the surgical controlling system, wherein said tool comprises at least one proximity sensor positioned on the outer circumference of the same.

It is another object of the present invention to disclose the surgical controlling system, wherein said instructions comprise a predetermined set of rules selected from a group consisting of: most used tool rule, right tool rule, left tool rule, field of view rule, no fly zone rule, a route rule, environmental rule, operator input rule, proximity rule; collision prevention rule, history-based rule, tool-dependent allowed and restricted movements rule, preferred volume zone rule, preferred tool rule, movement detection rule, tagged tool rule, change of speed rule and any combination thereof.

It is another object of the present invention to disclose the surgical controlling system, wherein said route rule comprises a communicable database storing predefined route in which said at least one surgical tool is configured to move within said surgical environment; said predefined route comprises n 3D spatial positions of said at least one surgical tool; n is an integer greater than or equal to 2; said allowed movements are movements in which said at least one surgical tool is located substantially in at least one of said n 3D spatial positions of said predefined route, and said restricted movements are movements in which said location of said at least one surgical tool is substantially different from said n 3D spatial positions of said predefined route.

It is another object of the present invention to disclose the surgical controlling system, wherein said environmental rule comprises a comprises a communicable database; said communicable database configured to receive at least one real-time image of said surgical environment and is configured to perform real-time image processing of the same and to determine the 3D spatial position of hazards or obstacles in said surgical environment; said environmental rule is configured to determine said allowed and restricted movements according to said hazards or obstacles in said surgical environment, such that said restricted movements are movements in which said at least one surgical tool is located substantially in at least one of said 3D spatial positions, and said allowed movements are movements in which the location of said at least one surgical tool is substantially different from said 3D spatial positions.

It is another object of the present invention to disclose the surgical controlling system, wherein said hazards or obstacles in said surgical environment are selected from a group consisting of tissue, a surgical tool, an organ, an endoscope and any combination thereof.

It is another object of the present invention to disclose the surgical controlling system, wherein said operator input rule comprises a communicable database; said communicable database is configured to receive an input from the operator of said system regarding said allowed and restricted movements of said at least one surgical tool.

It is another object of the present invention to disclose the surgical controlling system, wherein said input comprises n 3D spatial positions; n is an integer greater than or equal to 2; wherein at least one of which is defined as allowed location and at least one of which is defined as restricted location, such that said allowed movements are movements in which said at least one surgical tool is located substantially in at least one of said n 3D spatial positions, and said restricted movements are movements in which the location of said at least one surgical tool is substantially different from said n 3D spatial positions.

It is another object of the present invention to disclose the surgical controlling system, wherein said input comprises at least one rule according to which allowed and restricted movements of said at least one surgical tool are determined, such that the spatial position of said at least one surgical tool is controlled by said controller according to said allowed and restricted movements.

It is another object of the present invention to disclose the surgical controlling system, wherein said operator input rule converts an allowed movement to a restricted movement and a restricted movement to an allowed movement.

It is another object of the present invention to disclose the surgical controlling system, wherein said proximity rule is configured to define a predetermined distance between at least two surgical tools; said allowed movements are movements which are within the range or out of the range of said predetermined distance, and said restricted movements are movements which are out of the range or within the range of said predetermined distance.

It is another object of the present invention to disclose the surgical controlling system, wherein said proximity rule is configured to define a predetermined angle between at least three surgical tools; said allowed movements are movements which are within the range or out of the range of said predetermined angle, and said restricted movements which are out of the range or within the range of said predetermined angle.

It is another object of the present invention to disclose the surgical controlling system, wherein said collision prevention rule is configured to define a predetermined distance between said at least one surgical tool and an anatomical element within said surgical environment; said allowed movements are movements which are in a range that is larger than said predetermined distance, and said restricted movements are movements which is in a range that is smaller than said predetermined distance.

It is another object of the present invention to disclose the surgical controlling system, wherein said anatomical element is selected from a group consisting of tissue, organ, another surgical tool and any combination thereof.

It is another object of the present invention to disclose the surgical controlling system, wherein said right tool rule is configured to determine said allowed movement of said endoscope according to the movement of the surgical tool positioned to right of said endoscope; further wherein said left tool rule is configured to determine said allowed movement of said endoscope according to the movement of the surgical tool positioned to left of said endoscope.

It is another object of the present invention to disclose the surgical controlling system, wherein said tagged tool rule comprises means configured to tag at least one surgical tool within said surgical environment and to determine said allowed movement of said endoscope so as to constantly track the movement of said tagged surgical tool.

It is another object of the present invention to disclose the surgical controlling system, wherein said field of view rule comprises a communicable database comprising n 3D spatial positions; n is an integer greater than or equal to 2; the combination of all of said n 3D spatial positions provides a predetermined field of view; said field of view rule is configured to determine said allowed movement of said endoscope within said n 3D spatial positions so as to maintain a constant field of view, such that said allowed movements are movements in which said endoscope is located substantially in at least one of said n 3D spatial positions, and said restricted movements are movements in which the location of said endoscope is substantially different from said n 3D spatial positions.

It is another object of the present invention to disclose the surgical controlling system, wherein said preferred volume zone rule comprises a communicable database comprising n 3D spatial positions; n is an integer greater than or equal to 2; said n 3D spatial positions provides said preferred volume zone; said preferred volume zone rule is configured to determine said allowed movement of said endoscope within said n 3D spatial positions and restricted movement of said endoscope outside said n 3D spatial positions, such that said allowed movements are movements in which said endoscope is located substantially in at least one of said n 3D spatial positions, and said restricted movements are movements in which the location of said endoscope is substantially different from said n 3D spatial positions.

It is another object of the present invention to disclose the surgical controlling system, wherein said preferred tool rule comprises a communicable database, said database stores a preferred tool; said preferred tool rule is configured to determine said allowed movement of said endoscope to constantly track the movement of said preferred tool.

It is another object of the present invention to disclose the surgical controlling system, said no fly zone rule comprises a communicable database comprising n 3D spatial positions; n is an integer greater than or equal to 2; said n 3D spatial positions define a predetermined volume within said surgical environment; said no fly zone rule is configured to determine said restricted movement if said movement is within said no fly zone and allowed movement if said movement is outside said no fly zone, such that said restricted movements are movements in which said at least one of said surgical tool is located substantially in at least one of said n 3D spatial positions, and said allowed movements are movements in which the location of said at least one endoscope is substantially different from said n 3D spatial positions.

It is another object of the present invention to disclose the surgical controlling system, wherein said most used tool rule comprises a communicable database counting the amount of movement of each said surgical tool; said most used tool rule is configured to constantly position said endoscope to track the movement of the most moved surgical tool.

It is another object of the present invention to disclose the surgical controlling system, wherein said system further comprises a maneuvering subsystem communicable with said controller, said maneuvering subsystem is configured to spatially reposition said at least one surgical tool during a surgery according to said predetermined set of rules; further wherein said system is configured to alert the physician of said restricted movement of said at least one surgical tool.

It is another object of the present invention to disclose the surgical controlling system, wherein said alert is selected from a group consisting of audio signaling, voice signaling, light signaling, flashing signaling and any combination thereof.

It is another object of the present invention to disclose the surgical controlling system, wherein said allowed movement is permitted by said controller and said restricted movement is denied by said controller.

It is another object of the present invention to disclose the surgical controlling system, wherein said history-based rule comprises a communicable database storing each 3D spatial position of each said surgical tool, such that each movement of each surgical tool is stored; said history-based rule is configured to determine said allowed and restricted movements according to historical movements of said at least one surgical tool, such that said allowed movements are movements in which said at least one surgical tool is located substantially in at least one of said 3D spatial positions, and said restricted movements are movements in which the location of said at least one surgical tool is substantially different from said n 3D spatial positions.

It is another object of the present invention to disclose the surgical controlling system, wherein said tool-dependent allowed and restricted movements rule comprises a communicable database; said communicable database is configured to store predetermined characteristics of at least one of said surgical tool; said tool-dependent allowed and restricted movements rule is configured to determine said allowed and restricted movements according to said predetermined characteristics of said surgical tool; such that allowed movements are movements of said endoscope which track said surgical tool having said predetermined characteristics.

It is another object of the present invention to disclose the surgical controlling system, wherein said predetermined characteristics of said surgical tool are selected from a group consisting of: physical dimensions, structure, weight, sharpness, and any combination thereof.

It is another object of the present invention to disclose the surgical controlling system, wherein said movement detection rule comprises a communicable database comprising the real-time 3D spatial positions of each said surgical tool; said movement detection rule is configured to detect movement of said at least one surgical tool when a change in said 3D spatial positions is received, such that said allowed movements are movements in which said endoscope is re-directed to focus on said moving surgical tool.

It is another object of the present invention to disclose the surgical controlling system, further comprising a maneuvering subsystem communicable with said controller, said maneuvering subsystem is configured to spatially reposition said at least one surgical tool during a surgery according to said predetermined set of rules, such that if said movement of said at least one surgical tool is a restricted movement, said maneuvering subsystem prevents said movement.

It is another object of the present invention to disclose the surgical controlling system, wherein said at least one location estimating means comprises at least one endoscope configured to acquire real-time images of said surgical environment within said human body; and at least one surgical instrument spatial location software configured to receive said real-time images of said surgical environment and to estimate said 3D spatial position of said at least one surgical tool.

It is another object of the present invention to disclose the surgical controlling system, wherein said at least one location estimating means comprises (a) at least one element selected from a group consisting of optical imaging means, radio frequency transmitting and receiving means, at least one mark on said at least one surgical tool and any combination thereof; and, (b) at least one surgical instrument spatial location software configured to estimate said 3D spatial position of said at least one surgical tool by means of said element.

It is another object of the present invention to disclose the surgical controlling system, wherein said at least one location estimating means is an interface subsystem between a surgeon and said at least one surgical tool, the interface subsystem comprising:

a. at least one array comprising N regular or pattern light sources, where N is a positive integer;
b. at least one array comprising M cameras, each of the M cameras, where M is a positive integer;
c. optional optical markers and means for attaching the optical marker to the at least one surgical tool; and;
d. a computerized algorithm operable via the controller, the computerized algorithm configured to process images received by each camera of each of the M cameras and to calculate therefrom the position of each of the tools, and further configured to provide automatically the results of the calculation to the human operator of the interface.

It is another object of the present invention to disclose a method of using a surgical controlling system, comprising steps of:

a. providing a surgical controlling system comprising:
   i. at least one surgical tool configured to be inserted into a surgical environment of a human body for assisting a surgical procedure;
   ii. at least one location estimating means configured for real-time localization of the 3D spatial position of said at least one surgical tool at any given time t;
   iii. at least one movement detection means communicable with a movement's database and with said location estimating means; said movement's database is configured to store said 3D spatial position of said at least one surgical tool at time $t_f$ and at time $t_0$; where $t_f > t_0$; said movement detection means is configured to detect movement of said at least one surgical tool if the 3D spatial position of said at least one surgical tool at time $t_f$ is different than said 3D spatial position of said at least one surgical tool at time $t_0$; and,
  iv. a controller having a processing means communicable with a controller's database, said controller configured to control the spatial position of said at least one surgical tool; said controller's database is in communication with said movement detection means;
  v. input receiving means configured to receive input of at least one location within said surgical environment of said human body; and
  vi. at least one display configured to real time provide an image of at least a portion of said surgical environment;
b. inserting at least one said surgical tool into said surgical environment;
c. displaying said at least a portion of said surgical environment;
d. receiving input of at least one location within said surgical environment of said human body;
e. estimating the 3D spatial position of at least one said surgical tool; and
f. directing and moving said surgical tool to said location via instructions provided by said controller
wherein said location is real time updated on said display as said at least one surgical tool is moved
additionally comprising steps of selecting said input receiving means to be at least one touchscreen in wired or wireless communication with said controller, configuring said touchscreen to display an image of at least a portion of said surgical environment of said human body and configuring said touchscreen to receive input of at least one location within said surgical environment of said human body.

It is another object of the present invention to disclose the method, additionally comprising steps of receiving said input by providing said at least one touchscreen, displaying said image of at least a portion of said surgical environment via said touchscreen; and determining said location within said surgical environment of said human body from pressure on a portion of said touchscreen.

It is another object of the present invention to disclose the method, additionally comprising step of selecting said portion of said touchscreen to be that which displays the image of said location.

It is another object of the present invention to disclose the method, additionally comprising steps of displaying a direction indicator on said portion of said touchscreen, and selecting said direction indicator from a group consisting of: an arrow pointing in a predefined direction, a line pointing in a predefined direction, a pointer pointing in a predefined direction, the word "left", the word "right" the word "up", the word "down", the word "forward", the word "back", the word "zoom", the word "in", the word "out", and any combination thereof.

It is another object of the present invention to disclose the method, additionally comprising step of selecting said input receiving means from a group consisting of: (a) at least one first camera, in wired or wireless communication with said controller, configured to detect movement of an eye; and (b) at least one second camera, in wired or wireless communication with said controller, configured to detect movement of a hand, and any combination thereof.

It is another object of the present invention to disclose the method, additionally comprising step of receiving said input in a manner selected from a group consisting of: (a) providing said at least one first camera and determining said movement of said eye; and (b) providing said at least one second camera and determining said movement of said hand.

It is another object of the present invention to disclose the method, additionally comprising step of determining, for said movement of said hand, at least one of a group consisting of: direction of movement of said hand and speed of movement of said hand.

It is another object of the present invention to disclose the method, additionally comprising step of selecting said direction of movement of said hand from a group consisting of: left, right, up, down, forward, back, and any combination thereof.

It is another object of the present invention to disclose the method, additionally comprising step of determining, for said movement of said eye, at least one of a group consisting of: direction of movement of said eye, speed of movement of said eye, closing of said eye.

It is another object of the present invention to disclose the method, additionally comprising step of selecting said direction of movement of said eye from a group consisting of: left, right, up, down, and any combination thereof.

It is another object of the present invention to disclose the method, additionally comprising at least one of the following steps: (a) additionally providing an endoscope for said system; and providing at least one real-time image of said surgical environment by means of said endoscope; (b) selecting at least one of said surgical tools to be an endoscope and providing at least one real-time image of said surgical environment by means of said endoscope.

It is another object of the present invention to disclose the method, additionally comprising step of positioning at least one proximity sensor on the outer circumference of said tool.

It is another object of the present invention to disclose the method, additionally comprising step of selecting said instructions from a predetermined set of rules selected from a group consisting of: most used tool rule, right tool rule, left tool rule, field of view rule, no fly zone rule, a route rule, environmental rule, operator input rule, proximity rule; collision prevention rule, history-based rule, tool-dependent allowed and restricted movements rule, preferred volume zone rule, preferred tool rule, movement detection rule, tagged tool rule, change of speed rule and any combination thereof.

It is another object of the present invention to disclose the method, wherein said route rule comprises steps of: providing a communicable database; storing a predefined route in which said at least one surgical tool is configured to move within said surgical environment; comprising said predefined route of n 3D spatial positions of said at least one surgical tool, n is an integer greater than or equal to 2; said allowed movements are movements in which said at least one surgical tool is located substantially in at least one of said n 3D spatial positions of said predefined route, and said restricted movements are movements in which said location of said at least one surgical tool is substantially different from said n 3D spatial positions of said predefined route.

It is another object of the present invention to disclose the method, wherein said environmental rule comprises steps of: providing a communicable database; receiving at least one real-time image of said surgical environment in said communicable database; performing real-time image processing of the same and determining the 3D spatial position of hazards or obstacles in said surgical environment; determining said allowed and restricted movements according to said hazards or obstacles in said surgical environment, such that said restricted movements are movements in which said at least one surgical tool is located substantially in at least one of said 3D spatial positions, and said allowed movements are movements in which the location of said at least one surgical tool is substantially different from said 3D spatial positions.

It is another object of the present invention to disclose the method, additionally comprising step of selecting said hazards or obstacles in said surgical environment from a group consisting of tissue, a surgical tool, an organ, an endoscope and any combination thereof.

It is another object of the present invention to disclose the method, wherein said operator input rule comprises steps of: providing a communicable database; and receiving input from an operator of said system regarding said allowed and restricted movements of said at least one surgical tool.

It is another object of the present invention to disclose the method, additionally comprising steps of: comprising said input of n 3D spatial positions, n is an integer greater than or equal to 2; defining at least one of said spatial positions as an allowed location; defining at least one of said spatial positions as a restricted location; such that said allowed movements are movements in which said at least one surgical tool is located substantially in at least one of said n 3D spatial positions, and said restricted movements are movements in which the location of said at least one surgical tool is substantially different from said n 3D spatial positions.

It is another object of the present invention to disclose the method, additionally comprising steps of: comprising said input of at least one rule according to which allowed and restricted movements of said at least one surgical tool are determined, and controlling the spatial position of said at least one surgical tool by said controller according to said allowed and restricted movements.

It is another object of the present invention to disclose the method, wherein said operator input rule comprises steps of: converting an allowed movement to a restricted movement and converting a restricted movement to an allowed movement.

It is another object of the present invention to disclose the method, wherein said proximity rule comprises step of: defining a predetermined distance between at least two surgical tools; said allowed movements are movements which are within the range or out of the range of said predetermined distance, and said restricted movements are movements which are out of the range or within the range of said predetermined distance.

It is another object of the present invention to disclose the method, wherein said proximity rule comprises step of: defining a predetermined angle between at least three surgical tools; said allowed movements are movements which are within the range or out of the range of said predetermined angle, and said restricted movements are movements which are out of the range or within the range of said predetermined angle.

It is another object of the present invention to disclose the method, wherein said collision prevention rule comprises step of: defining a predetermined distance between said at least one surgical tool and an anatomical element within said surgical environment; said allowed movements are movements which are in a range that is larger than said predetermined distance, and said restricted movements are movements which is in a range that is smaller than said predetermined distance.

It is another object of the present invention to disclose the method, additionally comprising step of selecting said anatomical element from a group consisting of tissue, organ, another surgical tool and any combination thereof.

It is another object of the present invention to disclose the method, wherein said right tool rule comprises step of: determining said allowed movement of said endoscope according to the movement of the surgical tool positioned to right of said endoscope; further wherein said left tool rule comprises step of: determining said allowed movement of said endoscope according to the movement of the surgical tool positioned to left of said endoscope.

It is another object of the present invention to disclose the method, wherein said tagged tool rule comprises steps of: tagging at least one surgical tool within said surgical environment and determining said allowed movements of said endoscope to be movements that constantly track the movement of said tagged surgical tool.

It is another object of the present invention to disclose the method, wherein said field of view rule comprises steps of: providing a communicable database comprising n 3D spatial positions; n is an integer greater than or equal to 2; generating a field of view from the combination of all of said n 3D spatial positions; maintaining a constant field of view by determining said allowed movement of said endoscope to be within said n 3D spatial positions, such that said allowed movements are movements in which said endoscope is located substantially in at least one of said n 3D spatial positions, and said restricted movements are movements in which the location of said endoscope is substantially different from said n 3D spatial positions.

It is another object of the present invention to disclose the method, wherein said preferred volume zone rule comprises steps of: providing a communicable database comprising n 3D spatial positions; n is an integer greater than or equal to 2; generating said preferred volume zone from said n 3D spatial positions; determining said allowed movement of said endoscope to be within said n 3D spatial positions and said restricted movement of said endoscope to be outside said n 3D spatial positions, such that said allowed movements are movements in which said endoscope is located substantially in at least one of said n 3D spatial positions, and said restricted movements are movements in which the location of said endoscope is substantially different from said n 3D spatial positions.

It is another object of the present invention to disclose the method, wherein said preferred tool rule comprises steps of: providing a communicable database, storing a preferred tool in said database; and determining said allowed movement of said endoscope so as to constantly track the movement of said preferred tool.

It is another object of the present invention to disclose the method, wherein said no fly zone rule comprises steps of: providing a communicable database comprising n 3D spatial positions, n is an integer greater than or equal to 2; defining a predetermined volume within said surgical environment from said n 3D spatial positions; determining said restricted movement to be said movement within said no fly zone; determining said allowed movement to be said movement outside said no fly zone, such that said restricted movements are movements in which said at least one of said surgical tool is located substantially in at least one of said n 3D spatial positions, and said allowed movements are movements in which the location of said at least one endoscope is substantially different from said n 3D spatial positions.

It is another object of the present invention to disclose the method, wherein said most used tool rule comprises steps of: providing a communicable database; counting the amount of movement of each said surgical tool; constantly positioning said endoscope to track movement of the most moved surgical tool.

It is another object of the present invention to disclose the method, additionally comprising steps of providing a maneuvering subsystem communicable with said controller, spatially repositioning said at least one surgical tool during a surgery according to said predetermined set of rules; and alerting the physician of said restricted movement of said at least one surgical tool.

It is another object of the present invention to disclose the method, additionally comprising step of selecting said alert from a group consisting of: audio signaling, voice signaling, light signaling, flashing signaling and any combination thereof.

It is another object of the present invention to disclose the method, additionally comprising steps of defining said allowed movement as a movement permitted by said controller and defining said restricted movement as a movement denied by said controller.

It is another object of the present invention to disclose the method, wherein said history-based rule comprises steps of: providing a communicable database storing each 3D spatial position of each said surgical tool, such that each movement of each surgical tool is stored; determining said allowed and restricted movements according to historical movements of said at least one surgical tool, such that said allowed movements are movements in which said at least one surgical tool is located substantially in at least one of said 3D spatial positions, and said restricted movements are movements in which the location of said at least one surgical tool is substantially different from said n 3D spatial positions.

It is another object of the present invention to disclose the method, wherein said tool-dependent allowed and restricted movements rule comprises steps of: providing a communicable database; storing predetermined characteristics of at least one said surgical tool; determining said allowed and restricted movements according to said predetermined characteristics of said surgical tool; such that allowed movements are movements of said endoscope which track said surgical tool having said predetermined characteristics.

It is another object of the present invention to disclose the method, additionally comprising step of selecting said predetermined characteristics of said surgical tool from a group consisting of: physical dimensions, structure, weight, sharpness, and any combination thereof.

It is another object of the present invention to disclose the method, wherein said movement detection rule comprises steps of: providing a communicable database comprising the real-time 3D spatial positions of each said surgical tool; detecting movement of said at least one surgical tool when a change in said 3D spatial positions is received, such that said allowed movements are movements in which said endoscope is re-directed to focus on said moving surgical tool.

It is another object of the present invention to disclose the method, additionally comprising steps of providing a maneuvering subsystem communicable with said controller, spatially repositioning said at least one surgical tool during a surgery according to said predetermined set of rules, such that if said movement of said at least one surgical tool is a restricted movement, said maneuvering subsystem prevents said movement.

It is another object of the present invention to disclose the method, additionally comprising steps of comprising said at least one location estimating means of at least one endoscope configured to acquire real-time images of said surgical environment within said human body; providing at least one surgical instrument spatial location software; receiving said real-time images of said surgical environment from said endoscope and estimating said 3D spatial position of said at least one surgical tool using said spatial location software.

It is another object of the present invention to disclose the method, additionally comprising step of providing said at least one location estimating means comprising (a) at least one element selected from a group consisting of optical imaging means, radio frequency transmitting and receiving means, at least one mark on said at least one surgical tool and any combination thereof; and, (b) at least one surgical instrument spatial location software configured to estimate said 3D spatial position of said at least one surgical tool by means of said element.

It is another object of the present invention to disclose the method, additionally comprising step of selecting said at least one location estimating means to be an interface subsystem between a surgeon and said at least one surgical tool, the interface subsystem comprising:
  a. at least one array comprising N regular or pattern light sources, where N is a positive integer;
  b. at least one array comprising M cameras, each of the M cameras, where M is a positive integer;
  c. optional optical markers and means for attaching the optical marker to the at least one surgical tool; and;
  d. a computerized algorithm operable via the controller, the computerized algorithm configured to process images received by each camera of each of the M cameras and to calculate therefrom the position of each of the tools, and further configured to provide automatically the results of the calculation to the human operator of the interface.

BRIEF DESCRIPTION OF THE FIGURES

In order to understand the invention and to see how it may be implemented in practice, and by way of non-limiting example only, with reference to the accompanying drawing, in which.

DETAILED DESCRIPTION OF THE PREFERRED EMBODIMENTS

Figure 1:
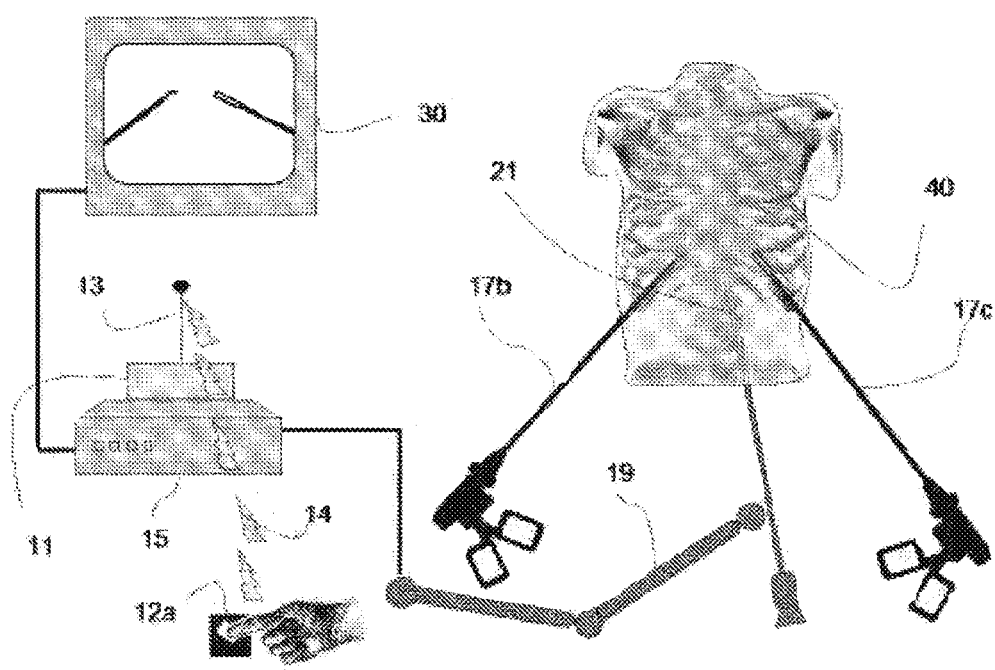
FIG. 1 illustrates one embodiment of the present invention.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for directing a laparoscopic system by means of a touchscreen.

The term 'wink' refers hereinafter to closure of a single eye.

The term 'blink' refers hereinafter to substantially simultaneous closure of both eyes.

The term 'toggle' refers hereinafter to switching between one tagged surgical tool to another.

The term 'surgical environment' refers hereinafter to any anatomical part within the human body which may be in surrounding a surgical instrument. The environment may comprise: organs, body parts, walls of organs, arteries, veins, nerves, a region of interest, or any other anatomical part of the human body.

The term 'voice receiving means' refers hereinafter to any means configured for detect sound within a predefined volume.

The term 'surgical tool' refers hereinafter to any tool used in minimal invasive procedures. It could be a rigid tool, an articulating tool or any combination thereof.

The term 'endoscope' refers hereinafter to any means configured for looking inside the body for medical reasons. This may be any instrument used to examine the interior of a hollow organ or cavity of the body. The endoscope may also refer to any kind of a laparascope. It should be pointed that the following description may refer to an endoscope as a surgical tool.

The term 'region of interest' refers hereinafter to any region within the human body which may be of interest to the operator of the system of the present invention. The region of interest may be, for example, an organ to be operated on, a restricted area to which approach of a surgical instrument is restricted, a surgical instrument, or any other region within the human body.

The term 'spatial position' refers hereinafter to a predetermined spatial location and/or orientation of an object (e.g., the spatial location of the endoscope, the angular orientation of the endoscope, and any combination thereof).

The term 'prohibited area' refers hereinafter to a predetermined area to which a surgical tool (e.g., an endoscope) is prohibited to be spatially positioned in.

The term 'preferred area' refers hereinafter to predetermined area to which a surgical tool (e.g., an endoscope) is allowed and/or preferred to be spatially positioned in.

The term 'automated assistant' refers hereinafter to any mechanical device (including but not limited to a robotic device) that can maneuver and control the position of a surgical or endoscopic instrument, and that can in addition be configured to receive commands from a remote source.

The term 'tool' or 'surgical instrument' refers hereinafter to any instrument or device introducible into the human body. The term may refer to any location on the tool. For example it can refer to the tip of the same, the body of the same and any combination thereof.

It should be further pointed that the following description may refer to a surgical tool/instrument as an endoscope.

The term 'provide' refers hereinafter to any process (visual, tactile, or auditory) by which an instrument, computer, controller, or any other mechanical or electronic device can report the results of a calculation or other operation to a human operator.

The term 'automatic' or 'automatically' refers to any process that proceeds without the necessity of direct intervention or action on the part of a human being.

The term 'allowed movement' refers hereinafter to any movement of a surgical tool which is permitted according to a predetermined set of rules.

The term 'restricted movement' refers hereinafter to any movement of a surgical tool which is forbidden according to a predetermined set of rules. For example, one rule, according to the present invention, provides a preferred volume zone rule which defines a favored zone within the surgical environment. Thus, according to the present invention an allowed movement of a surgical tool or the endoscope is a movement which maintains the surgical tool within the favored zone; and a restricted movement of a surgical tool is a movement which extracts (or moves) the surgical tool outside the favored zone.

The term 'time step' refers hereinafter to the working time of the system. At each time step, the system receives data from sensors and commands from operators and processes the data and commands and executes actions. The time step size is the elapsed time between time steps.

The term 'proximity sensor' hereinafter refers to a sensor able to detect the presence of nearby objects without physical contact. Proximity sensors are sometimes referred to as 'force sensors'. A proximity sensor often emits an electromagnetic field or a beam of electromagnetic radiation (infrared, for instance), and looks for changes in the field or return signal. The object being sensed is often referred to as the proximity sensor's target. Different proximity sensor targets demand different sensors. For example, a capacitive photoelectric sensor might be suitable for a plastic target; an inductive proximity sensor always requires a metal target. Proximity sensors can be introduced into the body and used for detecting metal fragments during surgery. See, for example, Sakthivel, M., *A new inductive proximity sensor as a guiding tool for removing metal shrapnel during surgery*, Instrumentation and Measurement Technology Conference (I2MTC), 2013 IEEE International, pp. 53-57. ISSN: 1091-5281, print ISBN: 978-1-4673-4621-4. INSPEC Accession Number: 13662555.

Laparoscopic surgery, also called minimally invasive surgery (MIS), is a modern surgical technique in which operations in the abdomen are performed through small incisions (usually 0.5-1.5 cm) as compared to larger incisions needed in traditional surgical procedures. The key element in laparoscopic surgery is the use of a laparoscope, which is a device configured for viewing the scene within the body, at the distal end of the laparoscope. Either an imaging device is placed at the end of the laparoscope, or a rod lens system or fiber optic bundle is used to direct this image to the proximal end of the laparoscope. Also attached is a light source to illuminate the operative field, inserted through a 5 mm or 10 mm cannula or trocar to view the operative field.

The abdomen is usually injected with carbon dioxide gas to create a working and viewing space. The abdomen is essentially blown up like a balloon (insufflated), elevating the abdominal wall above the internal organs like a dome. Within this space, various medical procedures can be carried out.

In many cases, the laparoscope cannot view the entire working space within the body, so the laparoscope is repositioned to allow the surgeon to view regions of interest within the space. In some laparoscopic system, this requires the surgeon to instruct an assistant to manually move the laparoscope. In other systems, the surgeon himself instructs the laparoscope to move, typically by pressing or sliding a button. Although this method is less error-prone than instructing an assistant to move the laparoscope manually, it does require additional equipment (the controller) and also requires good hand-eye coordination to ensure that the instrument follows the correct path.

In some embodiments of the device of the present invention, a touchscreen is used as the display screen on which the image of the field of view of the laparoscope is displayed. In order to direct the laparoscope, the surgeon touches the portion of the image toward which he wants the laparoscope to move and automatic control software controls the motion of the laparoscope towards the goal. Thus, in preferred embodiments, the surgeon need not concern himself with the mechanics of repositioning; a brief touch on the display screen and he can return his hand to the instrument while the laparoscope automatically repositions itself.

In preferred embodiments of devices with a touchscreen, the surgeon directs the instrument to the desired location either by touching the portion of the screen showing the image of the desired location or by drawing, on the screen, the desired path for the instrument to follow. In preferred variants, the system provides both options (touch to direct and draw to direct).

As an example of the first, to direct the laparoscope to put the tip of the appendix in the center of the screen, the surgeon would touch the image of the tip of appendix on the screen. In these embodiments, the surgeon touches the screen only briefly; continued pressure is not needed to direct the laparoscope to the desired position.

As an example of the second, the surgeon wants the tip of the appendix in the center of the screen, but the "straight line" path from the current location of the instrument to the tip of the appendix would pass directly over an area of considerable inflammation, which the surgeon wants to avoid. Therefore, the surgeon traces a path on the screen for the instrument to follow which circles around the area of inflammation.

In some embodiments of devices with a touchscreen, the screen contains at least one graphical direction indicator, which can be at least one arrow, line or pointer or, preferably, a direction rose with 4, 8 or 16 indicators. In some variants of these embodiments, the surgeon touches the appropriate indicator, for non-limiting example, the one pointing at 45° clockwise from the vertical, and the laparoscope moves so that the center of its field of view moves towards the upper right portion of the image. In these embodiments, the surgeon needs to keep his hand on the touchscreen until the maneuver is complete.

In other variants of embodiments with graphical indicators, the indicator comprises a direction rose, the surgeon touches a position anywhere on the graphical indicator and the laparoscope moves so that the center of its field of view moves towards the direction indicated by the position of the touch. For example, if the surgeon touches a position 55° clockwise from the vertical, the laparoscope will move so that the center of its field of view moves towards the upper right portion of the image, at an angle 55° clockwise from the vertical. In these embodiments, the surgeon needs to keep his hand on the touchscreen until the maneuver is complete.

In other variants of embodiments with graphical indicators, the location of the touch on the indicator defines the speed at which the center of the field of view moves. For non-limiting example, the further from the center of the direction rose, the faster the motion.

In yet other embodiments of devices with a touchscreen, the direction of motion is indicated by words appearing on the screen such as, but not limited to, left, right, up, down, forward, back, zoom, zoom in, zoom out, and any combination thereof.

Combinations of the above embodiments will be obvious to one skilled in the art.

Many other means of indication direction of movement via a touchscreen will be obvious to one skilled in the art.

In yet other embodiments, voice commands are used to direct the endoscope. In such embodiments, the direction of motion can be indicated by words spoken by the surgeon such as, but not limited to, left, right, up, down, forward, back, zoom, zoom in, zoom out, and any combination thereof.

In some variants of embodiments employing voice commands, the surgeon can provide an angular designation, such as, but not limited to, a numerical value or a compass rose designation. Non-limiting examples of numerical values include 60°, 75° clockwise, 30° west of north. Other examples will be obvious to one skilled in the art. Non-limiting examples of compass rose designations are north-northwest, NNW, and southeast by south.

In yet other embodiments, hand gestures are used to direct the surgical tool. For non-limiting example, a movement of the surgeon's hand in a given direction moves the field of view (FOV) of the surgical tool in the direction of the hand movement. Hand movements can be, for example, left, right, towards the surgeon (forward), away from the surgeon (back), up and down. The surgeon can also, for non-limiting example, cup or flatten the hand, or spread the fingers or bring them together. A non-limiting example of a set of hand movements is movement left or right to move the FOV left or right, movement up or down to move the FOV towards the top or bottom of the screen, and movement left or right to zoom an endoscope in or out. Many other sets of hand gestures will be obvious to one skilled in the art.

In embodiments where hand gestures direct the endoscope, cameras, preferably 3D cameras, and associated image processing software, as is known in the art, can be used to identify the hand movements.

In still other embodiments, the surgeon's eye movements are used to direct the endoscope. For non-limiting example, a movement of the surgeon's eye in a given direction moves the FOV of the endoscope in the direction of the eye movement. Eye movements can be, for example, left, right, up and down. The surgeon can also, for non-limiting example, blink (close both eyes briefly), wink (close one eye briefly), move his eyes rapidly from side to side, or roll his eyes. A non-limiting example of a set of eye movements is movement left or right to move the FOV left or right, movement up or down to move the FOV towards the top or bottom of the screen, a wink of the left eye to zoom in and a wink of the right eye to zoom out.

In one variant of winking to zoom, a single wink zooms by a predetermined amount, while a double wink initiates continuous zooming, to be terminated by a second double wink. In another variant, zooming is initiated by a wink and terminated by a blink. Many more variants will be obvious to one skilled in the art.

In embodiments where eye gestures direct the surgical tool, cameras, preferably 3D cameras, and associated image processing software, as is known in the art, can be used to identify the eye movements. In preferred variants of embodiments using eye movement, the camera(s) or other detectors of eye movement are mounted on a headband or helmet, so that they are in close proximity to the eye or eyes.

Any combination of methods of directing the surgical tool can be used. For non-limiting example, eye movements for left-right and forward-back movement of the surgical tool and hand gestures for zooming an endoscope. Many other combinations will be obvious to those skilled in the art.

It should be noted that, because the system is configured to track the movement of the surgical tool in real time, the position of the surgical tool as stored in the controlling system at all times is an accurate representation of the actual position of the surgical tool. Therefore, the system can accurately move the surgical tool to the location desired by the surgeon, as indicated by the surgeon's instructions (e.g., if, for non-limiting example, the surgeon touches the location in the image showing the tip of the liver, after the movement is completed, the tip of the liver will be substantially at the center of the FOV.

According to different embodiments of the present invention, the surgical controlling system comprises the following components:
a. at least one surgical tool configured to be inserted into a surgical environment of a human body for assisting a surgical procedure;
b. at least one location estimating means configured for real-time estimation and localization of the location (i.e., the 3D spatial position) of the at least one surgical tool at any given time t;
c. at least one movement detection means communicable with a movement-database and with said location estimating means; said movement-database is configured to store said 3D spatial position of said at least one surgical tool at time $t_f$ and at time $t_0$, where $t_f > t_0$; said movement detection means is configured to detect movement of said at least one surgical tool if the 3D spatial position of said at least one surgical tool at time $t_f$ is different than said 3D spatial position of said at least one surgical tool at time $t_0$; and,
d. a controller having a processing means communicable with a database, the controller configured to control the spatial position of the at least one surgical tool;
e. input receiving means configured to receive input of at least one location within said surgical environment of said human body; and
f. at least one display configured to real time provide an image of at least a portion of said surgical environment.

The input receiving means can be at least one touchscreen, or a camera or array of cameras to identify movement of at least one hand, or a camera or array of cameras to identify movement of at least one eye.

For the touchscreeen, the location(s) which is input is the location(s) indicated by pressure on a portion of the touchscreen, either the portion showing the image of the desired location, or a position on the portion comprising a direction indicator, or both.

For the camera(s) identifying hand movement, the direction of movement of the hand indicates the direction in which the surgical tool is to be moved and, similarly, for camera(s) identifying eye movement, the direction of movement of the eye or eyes indicates the direction in which the surgical tool is to be moved.

In directing the surgical controlling system, the controller needs to avoid body organs, and tools or other surgical equipment in the body cavity. Its speed should be controlled so that, on the one hand, the speed is low enough to make avoidance routine and to ensure that the instrument accurately reaches the desired location and, on the other hand, the speed needs to be great enough that maneuvers are accomplished in a reasonable time.

In order to facilitate control, a number of motion control rules have been implemented, as described hereinbelow.

It is within the scope of the present invention that the database is configured to store a predetermined set of rules according to which allowed and restricted movements of the at least one surgical tool are determined, such that the spatial position of the at least one surgical tool is controlled by the controller according to the allowed and restricted movements. In other words, each detected movement by said movement detection means of said at least one surgical tool is determined as either an allowed movement or as a restricted movement according to said predetermined set of rules.

Thus, the present invention stores the 3D spatial position of each surgical tool at a current at time $t_f$ and at time $t_0$; where $t_f > t_0$. If the 3D spatial position of said at least one surgical tool at time $t_f$ is different than said 3D spatial position of said at least one surgical tool at time $t_0$ movement of the tool is detected. Next the system analyses said movement according to said set of rule and process whether said movement is allowed movement or restricted movement.

According to one embodiment of the present invention, the system prevents said movement, if said movement is a restricted movement. Said movement prevention is obtained by controlling a maneuvering system which prevents the movement of said surgical tool.

According to one embodiment of the present invention, the system does not prevent said movement, (if said movement is a restricted movement), but merely signals/alerts the user (i.e., the physician) of said restricted movement.

According to another embodiment of the present invention, said surgical tool is an endoscope.

According to different embodiments of the present invention, the controller may provide a suggestion to the operator as to which direction the surgical tool has to move to or may be moved to.

Thus, according to a preferred embodiment of the present invention, the present invention provides a predetermined set of rules which define what is an "allowed movement" of any surgical tool within the surgical environment and what is a "restricted movement" of any surgical tool within the surgical environment.

According to some embodiments the system of the present invention comprises a maneuvering subsystem communicable with the controller, the maneuvering subsystem is configured to spatially reposition the at least one surgical tool during surgery according to the predetermined set of rules.

According to some embodiments, the controller may provide instructions to a maneuvering subsystem for spatially repositioning the location of the surgical tool. According to these instructions, only allowed movements of the surgical tool will be performed. Preventing restricted movements is performed by: detecting the location of the surgical tool; processing all current rules; analyzing the movement of the surgical tool and preventing the movement if the tool's movement is a restricted movement.

According to some embodiments, system merely alerts the physician of a restricted movement of at least one surgical tool (instead of preventing said restricted movement).

Alerting the physician of restricted movements (or, alternatively preventing a restricted movement) is performed by: detecting the location of the surgical tool; processing all current rules; analyzing the movement of the surgical tool and informing the surgeon (the user of the system) if the tool's movement is an allowed movement or a restricted movement.

Thus, according to a preferred embodiment of the present invention, if restricted movements are prevented, the same process (of detecting the location of the surgical tool; processing all current rules and analyzing the movement of the surgical tool) is followed except for the last movement, where the movement is prevented if the tool's movement is a restricted movement. The surgeon can also be informed that the movement is being prevented.

According to another embodiment, the above (alerting the physician and/or preventing the movement) is performed by detecting the location of the surgical tool and analyzing the surgical environment of the surgical tool. Following analysis of the surgical environment and detection of the location of the surgical tool, the system may assess all the risks which may follow a movement of the surgical tool in the predetermined direction. Therefore, each location in the surgical environment has to be analyzed so that any possible movement of the surgical tool will be classified as an allowed movement or a restricted movement.

According to one embodiment of the present invention, the location of each tool is determined using image processing means and the 3D spatial location of each tool is determined in real-time. It should be understood that the above mentioned "tool" may refer to the any location on the tool. For example, it can refer to the tip of the same, the body of the same and any combination thereof.

In some embodiments, avoidance of body organs is facilitated by means of a proximity sensor on the circumference of at least one tool. In these embodiments, if the distance between the tool and another object in the surgical environment, such as, but not limited to, an organ or another tool, is less than a predetermined distance, the proximity sensor activates, thereby notifying the control system that at least one tool is too close to another object in the surgical environment.

In some variants of embodiments with proximity sensors, the proximity sensor not only determined whether an object is within a predetermined distance of the sensor, it also determines, for objects within the predetermined distance, the distance between the sensor and the object.

Hereinbelow, determination of the 3D location of each tool includes determination by means of a proximity sensor as well as determination by means of image processing.

The predetermined set of rules which are the essence of the present invention are configured to take into consideration all the possible factors which may be important during the surgical procedure. The predetermined set of rules may comprise the following rules or any combination thereof:

a. a route rule;
b. an environment rule;
c. an operator input rule;
d. a proximity rule;
e. a collision prevention rule;
f. a history based rule;
g. a tool-dependent allowed and restricted movements rule.
h. a most used tool rule;
i. a right tool rule;
j. a left tool rule;
k. a field of view rule;
l. a no fly zone rule;
m. an operator input rule;
n. a preferred volume zone rule;
o. a preferred tool rule;
p. a movement detection rule, and
q. a tagged tool rule.

Thus, for example, the collision prevention rule defines a minimum distance below which two or more tools should not be brought together (i.e., there is minimum distance between two or more tools that should be maintained). If the movement of one tool will cause it to come dangerously close to another tool (i.e., the distance between them, after the movement, is smaller than the minimum distance defined by the collision prevention rule), the controller either alerts the user that the movement is a restricted movement or does not permit the movement.

It should be emphasized that all of the above (and the following disclosure) is enabled by constantly monitoring the surgical environment, and identifying and locating the 3D spatial location of each element/tool in the surgical environment.

The identification is provided by conventional means known to any skilled in the art (e.g., image processing, optical means etc.).

The following provides explanations for each of the above mentioned rules and its functions:

According to some embodiments, the route rule comprises a predefined route in which the at least one surgical tool is configured to move within the surgical environment; the allowed movements are movements in which the at least one surgical tool is located within the borders of the predefined route, and the restricted movements are movements in which the at least one surgical tool is located out of the borders of the predefined route. Thus, according to this embodiment, the route rule comprises a communicable database storing at least one predefined route in which the at least one surgical tool is configured to move within the surgical environment; the predefined route comprises n 3D spatial positions of the at least one surgical tool in the route; n is an integer greater than or equal to 2; allowed movements are movements in which the at least one surgical tool is located substantially in at least one of the n 3D spatial positions of the predefined route, and restricted movements are movements in which the location of the at least one surgical tool is substantially different from the n 3D spatial positions of the predefined route.

In other words, according to the route rule, each of the surgical tool's courses (and path in any surgical procedure) is stored in a communicable database. allowed movements are defined as movements in which the at least one surgical tool is located substantially in at least one of the stored routes; and restricted movements are movements in which the at least one surgical tool is in a substantially different location than any location in any stored route.

According to some embodiments, the environmental rule is configured to determine allowed and restricted movements according to hazards or obstacles in the surgical environment as received from an endoscope or other sensing means. Thus, according to this embodiment, the environmental rule comprises a comprises a communicable database; the communicable database is configured to received real-time images of the surgical environment and is configured to perform real-time image processing of the same and to determine the 3D spatial position of hazards or obstacles in the surgical environment; the environmental rule is configured to determine allowed and restricted movements according to hazards or obstacles in the surgical environment, such that restricted movements are movements in which at least one surgical tool is located substantially in at least one of the 3D spatial positions, and allowed movements are movements in which the location of at least one surgical tool is substantially different from the 3D spatial positions.

In other words, according to the environment rule, each element in the surgical environment is identified so as to establish which is a hazard or obstacle (and a path in any surgical procedure) and each hazard and obstacle (and path) is stored in a communicable database. restricted movements are defined as movements in which the at least one surgical tool is located substantially in the same location as that of the hazards or obstacles; and the allowed movements are movements in which the location of the at least one surgical tool is substantially different from that of all of the hazards or obstacles.

According to other embodiments, hazards and obstacles in the surgical environment are selected from a group consisting of tissues, surgical tools, organs, endoscopes and any combination thereof.

According to some embodiments, the operator input rule is configured to receive an input from the operator of the system regarding the allowed and restricted movements of the at least one surgical tool. Thus, according to this embodiment, the operator input rule comprises a communicable database; the communicable database is configured to receive an input from the operator of the system regarding allowed and restricted movements of the at least one surgical tool.

According to other embodiments, the input comprises n 3D spatial positions; n is an integer greater than or equal to 2; wherein at least one of which is defined as an allowed location and at least one of which is defined as a restricted location, such that the allowed movements are movements in which the at least one surgical tool is located substantially in at least one of the n 3D allowed spatial positions, and the restricted movements are movements in which the location of the at least one surgical tool is substantially different from the n 3D allowed spatial positions.

According to other embodiments, the input comprises at least one rule according to which allowed and restricted movements of the at least one surgical tool are determined, such that the spatial position of the at least one surgical tool is controlled by the controller according to the allowed and restricted movements.

According to other embodiments, the operator input rule can convert an allowed movement to a restricted movement and a restricted movement to an allowed movement.

According to some embodiments, the proximity rule is configured to define a predetermined distance between the at least one surgical tool and at least one another surgical tool; the allowed movements are movements which are within the range or out of the range of the predetermined distance, and the restricted movements which are out of the range or within the range of the predetermined distance; the allowed movements and the restricted movements are defined according to different ranges. Thus, according to this embodiment, the proximity rule is configured to define a predetermined distance between at least two surgical tools. In a preferred embodiment, the allowed movements are movements which are within the range of the predetermined distance, while the restricted movements which are out of the range of the predetermined distance. In another preferred embodiment, the allowed movements are movements which are out of the range of the predetermined distance, while the restricted movements are within the range of the predetermined distance It should be pointed out that the above mentioned distance can be selected from the following:
(a) the distance between the tip of the first tool and the tip of the second tool;
(b) the distance between the body of the first tool and the tip of the second tool;
(c) the distance between the body of the first tool and the body of the second tool;
(d) the distance between the tip of the first tool and the body of the second tool; and any combination thereof.

According to another embodiment, the proximity rule is configured to define a predetermined angle between at least three surgical tools; allowed movements are movements which are within the range or out of the range of the predetermined angle, and restricted movements are movements which are out of the range or within the range of the predetermined angle.

According to some embodiments, the collision prevention rule is configured to define a predetermined distance between the at least one surgical tool and an anatomical element within the surgical environment (e.g. tissue, organ, another surgical tool or any combination thereof); the allowed movements are movements which are in a range that is larger than the predetermined distance, and the restricted movements are movements which is in a range that is smaller than the predetermined distance.

According to another embodiment, the anatomical element is selected from a group consisting of tissue, organ, another surgical tool or any combination thereof.

According to some embodiments, the surgical tool is an endoscope. The endoscope is configured to provide real-time images of the surgical environment.

According to some embodiments, the right tool rule is configured to determine the allowed movement of the endoscope according to the movement of a surgical tool in a specified position in relation to the endoscope, preferably positioned to right of the same. According to this rule, the tool which is defined as the right tool is constantly tracked by the endoscope. According to some embodiments, the right tool is defined as the tool positioned to the right of the endoscope; according to other embodiments, any tool can be defined as the right tool. An allowed movement, according to the right tool rule, is a movement in which the endoscope field of view is moved to a location substantially the same as the location of the right tool, thereby tracking the right tool. A restricted movement, according to the right tool rule, is a movement in which the endoscope field of view is moved to a location substantially different from the location of the right tool.

According to some embodiments, the left tool rule is configured to determine the allowed movement of the endoscope according to the movement of a surgical tool in a specified position in relation to the endoscope, preferably positioned to left of the same. According to this rule, the tool which is defined as the left tool is constantly tracked by the endoscope. According to some embodiments, the left tool is defined as the tool positioned to the left of the endoscope; according to other embodiments, any tool can be defined as the left tool. An allowed movement, according to the left tool rule, is a movement in which the endoscope field of view is moved to a location substantially the same as the location of the left tool. A restricted movement, according to the left tool rule, is a movement in which the endoscope field of view is moved to a location substantially different from the location of the left tool.

According to some embodiments, the field of view rule is configured to define a field of view and maintain that field of view. The field of view rule is defined such that if the endoscope is configured to track a predetermined set of tools in a desired field of view, when one of those tools is no longer in the field of view, the rule instructs the endoscope to zoom out so as to reintroduce the tool into the field of view. Thus, according to this embodiment, the field of view rule comprises a communicable database comprising n 3D spatial positions; n is an integer greater than or equal to 2; the combination of all of the n 3D spatial positions provides a predetermined field of view; the field of view rule is configured to determine the allowed movement of the endoscope within the n 3D spatial positions so as to maintain a constant field of view, such that the allowed movements are movements in which the endoscope is located substantially in at least one of the n 3D spatial positions, and the restricted movements are movements in which the location of the endoscope is substantially different from the n 3D spatial positions.

Thus, according to another embodiment of the field of view rule, the field of view rule comprises a communicable database comprising n 3D spatial positions; n is an integer greater than or equal to 2; the combination of all of the n 3D spatial positions provides a predetermined field of view. The field of view rule further comprises a communicable database of m tools and the 3D spacial locations of the same, where m is an integer greater than or equal to 1 and where a tool can be a surgical tool, an anatomical element and any combination thereof. The combination of all of the n 3D spatial positions provides a predetermined field of view. The field of view rule is configured to determine allowed movement of the endoscope such that the m 3D spatial positions of the tools comprise at least one of the n 3D spatial positions of the field of view, and restricted movements are movements in which the 3D spatial position of at least one tool is substantially different from the n 3D spatial positions of the field of view.

According to another embodiment, the preferred volume zone rule comprises a communicable database comprising n 3D spatial positions; n is an integer greater than or equal to 2; the n 3D spatial positions provides the preferred volume zone; the preferred volume zone rule is configured to determine the allowed movement of the endoscope within the n 3D spatial positions and restricted movement of the endoscope outside the n 3D spatial positions, such that the allowed movements are movements in which the endoscope is located substantially in at least one of the n 3D spatial positions, and the restricted movements are movements in which the location of the endoscope is substantially different from the n 3D spatial positions. In other words, the preferred volume zone rule defines a volume of interest (a desired volume of interest), such that an allowed movement, according to the preferred volume zone rule, is a movement in which the endoscope (or any surgical tool) is moved to a location within the defined preferred volume. A restricted movement, according to the preferred volume zone rule, is a movement in which the endoscope (or any surgical tool) is moved to a location outside the defined preferred volume.

According to another embodiment, the preferred tool rule comprises a communicable database, the database stores a preferred tool; the preferred tool rule is configured to determine the allowed movement of the endoscope according to the movement of the preferred tool. In other words, the preferred tool rule defines a preferred tool (i.e., a tool of interest) that the user of the system wishes to track. An allowed movement, according to the preferred tool rule, is a movement in which the endoscope is moved to a location substantially the same as the location of the preferred tool. A restricted movement is a movement in which the endoscope is moved to a location substantially different from the location of the preferred tool. Thus, according to the preferred tool rule the endoscope constantly tracks the preferred tool, such that the field of view, as seen from the endoscope, is constantly the preferred tool. It should be noted that the user may define in said preferred tool rule to constantly track the tip of said preferred tool or alternatively, the user may define in said preferred tool rule to constantly track the body or any location on the preferred tool.

According to some embodiments, the no fly zone rule is configured to define a restricted zone into which no tool (or alternatively no predefined tool) is permitted to enter. Thus, according to this embodiment, the no fly zone rule comprises a communicable database comprising n 3D spatial positions; n is an integer greater than or equal to 2; the n 3D spatial positions define a predetermined volume within the surgical environment; the no fly zone rule is configured to determine a restricted movement if the movement is within the no fly zone and an allowed movement if the movement is outside the no fly zone, such that restricted movements are movements in which the at least one surgical tool is located substantially in at least one of the n 3D spatial positions, and the allowed movements are movements in which the location of the at least one surgical tool is substantially different from the n 3D spatial positions.

According to another embodiment, the most used tool rule is configured to define (either real-time, during the procedure or prior to the procedure) which tool is the most used tool (i.e., the tool which is moved the most during the procedure) and to instruct the maneuvering subsystem to constantly position the endoscope to track the movement of this tool. Thus, according to this embodiment, the most used tool rule comprises a communicable database counting the number of movements of each of the surgical tools; the most used tool rule is configured to constantly position the endoscope to track the movement of the surgical tool with the largest number of movements. In another embodiment of the most used tool rule, the communicable database measures the amount of movement of each of the surgical tools; the most used tool rule is configured to constantly position the endoscope to track the movement of the surgical tool with the largest amount of movement.

According to another embodiment, the system is configured to alert the physician of a restricted movement of at least one surgical tool. The alert can be audio signaling, voice signaling, light signaling, flashing signaling and any combination thereof.

According to another embodiment, an allowed movement is one permitted by the controller and a restricted movement is one denied by the controller.

According to another embodiment, the operator input rule is configured to receive an input from the operator of the system regarding allowed and restricted movements of the at least one surgical tool. In other words, the operator input rule receives instructions from the physician as to what can be regarded as allowed movements and what are restricted movements. According to another embodiment, the operator input rule is configured to convert an allowed movement to a restricted movement and a restricted movement to an allowed movement.

According to some embodiments, the history-based rule is configured to determine the allowed and restricted movements according to historical movements of the at least one surgical tool in at least one previous surgery. Thus, according to this embodiment, the history-based rule comprises a communicable database storing each 3D spatial position of each of the surgical tools, such that each movement of each surgical tool is stored; the history-based rule is configured to determine allowed and restricted movements according to historical movements of the at least one surgical tool, such that the allowed movements are movements in which the at least one surgical tool is located substantially in at least one of the 3D spatial positions, and the restricted movements are movements in which the location of the at least one surgical tool is substantially different from the n 3D spatial positions.

According to some embodiments, the tool-dependent allowed and restricted movements rule is configured to determine allowed and restricted movements according to predetermined characteristics of the surgical tool, where the predetermined characteristics of the surgical tool are selected from a group consisting of: physical dimensions, structure, weight, sharpness, and any combination thereof. Thus, according to this embodiment, the tool-dependent allowed and restricted movements rule comprises a communicable database; the communicable database is configured to store predetermined characteristics of at least one of the surgical tools; the tool-dependent allowed and restricted movements rule is configured to determine allowed and restricted movements according to the predetermined characteristics of the surgical tool.

According to another embodiment, the predetermined characteristics of the surgical tool are selected from a group consisting of: physical dimensions, structure, weight, sharpness, and any combination thereof.

According to this embodiment, the user can define, e.g., the structure of the surgical tool he wishes the endoscope to track. Thus, according to the tool-dependent allowed and restricted movements rule the endoscope constantly tracks the surgical tool having said predetermined characteristics as defined by the user.

According to another embodiment of the present invention, the movement detection rule comprises a communicable database comprising the real-time 3D spatial positions of each surgical tool; said movement detection rule is configured to detect movement of at least one surgical tool. When a change in the 3D spatial position of that surgical tool is received, allowed movements are movements in which the endoscope is re-directed to focus on the moving surgical tool.

According to another embodiment of the present invention, the tagged tool rule comprises means of tagging at least one surgical tool within the surgical environment such that, by maneuvering the endoscope, the endoscope is constantly directed to the tagged surgical tool. Thus, according to the tagged tool rule, the endoscope constantly tracks the preferred (i.e., tagged) tool, such that the field of view, as seen from the endoscope, is constantly maintained on the preferred (tagged) tool. It should be noted that the user can define the tagged tool rule to constantly track the tip of the preferred (tagged) tool, the body of the preferred (tagged) tool, or any other location on the preferred (tagged) tool.

According to another embodiment of the present invention, the system further comprises a maneuvering subsystem communicable with the controller. The maneuvering subsystem is configured to spatially reposition the at least one surgical tool during a surgery according to the predetermined set of rules.

According to some embodiments, the at least one location estimating means is at least one endoscope configured to acquire real-time images of a surgical environment within the human body for the estimation of the location of at least one surgical tool.

According to another embodiment, the location estimating means comprise at least one selected from a group consisting of optical imaging means, radio frequency transmitting and receiving means, at least one mark on at least one surgical tool and any combination thereof.

According to another embodiment, the at least one location estimating means is an interface subsystem between a surgeon and at least one surgical tool, the interface subsystem comprising (a) at least one array comprising N regular light sources or N pattern light sources, where N is a positive integer; (b) at least one array comprising M cameras, where M is a positive integer; (c) optional optical markers and means for attaching the optical markers to at least one surgical tool; and (d) a computerized algorithm operable via the controller, the computerized algorithm configured to process images received by each camera of each of the M cameras and to calculate therefrom the position of each of the tools, and further configured to provide automatically the results of the calculation to the human operator of the interface.

It is well known that surgery is a highly dynamic procedure with a constantly changing environment which depends on many variables. A non-limiting list of these variables includes, for example: the type of the surgery, the working space (e.g., with foreign objects, dynamic uncorrelated movements, etc), the type of tools used during the surgery, changing background, relative movements, dynamic procedures, dynamic input from the operator and the history of the patient. Therefore, there is need for a system which is able to integrate all the variables by weighting their importance and deciding to which spatial position the endoscope should be relocated.

The present invention can be also utilized to improve the interface between the operators (e.g., the surgeon, the operating medical assistant, the surgeon's colleagues, etc.). Moreover, the present invention can be also utilized to control and/or direct an automated maneuvering subsystem to focus the endoscope on an instrument selected by the surgeon, or to any other region of interest. This may be performed in order to estimate the location of at least one surgical tool during a surgical procedure.

The present invention also discloses a surgical tracking system which is configured to guide and relocate an endoscope to a predetermined region of interest in an automatic and/or a semi-automatic manner. This operation is assisted by an image processing algorithm(s) which is configured to analyze the received data from the endoscope in real time, and to assess the surgical environment of the endoscope.

According to an embodiment, the system comprises a "smart" tracking subsystem, which receives instructions from a maneuvering function f(t) (t is the time) as to where to direct the endoscope and which instructs the maneuvering subsystem to relocate the endoscope to the required area.

The maneuvering function f(t) receives, as input, output from at least two instructing functions $g_i(t)$, analyses their output and provides instruction to the "smart" tracking system (which eventually re-directs the endoscope).

According to some embodiments, each instructing function $g_i(t)$ is also given a weighting function, $\alpha_i(t)$.

The instructing functions $g_i(t)$ of the present invention are functions which are configured to assess the environment of the endoscope and the surgery, and to output data which guides the tracking subsystem for controlling the spatial position of the maneuvering subsystem and the endoscope. The instructing functions $g_i(t)$ may be selected from a group consisting of:

a. a tool detection function $g_1(t)$;
b. a movement detection function $g_2(t)$;
c. an organ detection function $g_3(t)$;
d. a collision detection function $g_4(t)$;
e. an operator input function $g_5(t)$;
f. a prediction function $g_6(t)$;
g. a past statistical analysis function $g_7(t)$;
h. a most used tool function $g_8(t)$;
i. a right tool function $g_9(t)$;
j. a left tool function $g_{10}(t)$;
k. a field of view function $g_{11}(t)$;
l. a preferred volume zone function $g_{12}(t)$;
m. a no fly zone function $g_{13}(t)$;
n. a proximity function $g_{14}(t)$;
o. a tagged tool function $g_{15}(t)$;
p. a preferred tool function $g_{16}(t)$.

Thus, for example, the maneuvering function f(t) receives input from two instructing functions: the collision detection function $g_4(t)$ (the function providing information whether the distance between two elements is smaller than a predetermined distance) and from the most used tool function $g_8(t)$ (the function counts the number of times each tool is moved during a surgical procedure and provides information as to whether the most moved or most used tool is currently moving). The output given from the collision detection function $g_4(t)$ is that a surgical tool is dangerously close to an organ in the surgical environment. The output given from the most used tool function $g_8(t)$ is that the tool identified statistically as the most moved tool is currently moving.

The maneuvering function f(t) then assigns each of the instructing functions with weighting functions $\alpha_i(t)$. For example, the most used tool function $g_8(t)$ is assigned with a greater weight than the weight assigned to the collision detection function $g_4(t)$.

After the maneuvering function f(t) analyses the information received from the instructing functions $g_i(t)$ and the weighting functions $\alpha_i(t)$ of each, the same outputs instructions to the maneuvering subsystem to re-direct the endoscope (either to focus on the moving tool or on the tool approaching dangerously close to the organ).

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.).

According to some embodiments, the surgical tracking subsystem comprises:

a. at least one endoscope configured to acquire real-time images of a surgical environment within the human body;
b. a maneuvering subsystem configured to control the spatial position of the endoscope during the laparoscopic surgery; and,
c. a tracking subsystem in communication with the maneuvering subsystem, configured to control the maneuvering subsystem so as to direct and modify the spatial position of the endoscope to a region of interest.

According to this embodiment, the tracking subsystem comprises a data processor. The data processor is configured to perform real-time image processing of the surgical environment and to instruct the maneuvering subsystem to modify the spatial position of the endoscope according to input received from a maneuvering function f(t); the maneuvering function f(t) is configured to (a) receive input from at least two instructing functions $g_i(t)$, where i is 1, ..., n and n≥2 and where t is time; i and n are integers; and (b) to output instructions to the maneuvering subsystem based on the input from the at least two instructing functions $g_i(t)$, so as to spatially position the endoscope to the region of interest.

According to one embodiment, the tool detection function $g_i(t)$ is configured to detect tools in the surgical environment. According to this embodiment, the tool detection function is configured to detect surgical tools in the surgical environment and to output instructions to the tracking subsystem to instruct the maneuvering subsystem to direct the endoscope to the detected surgical tools.

According to some embodiments, the functions $g_i(t)$ may rank the different detected areas in the surgical environment according to a ranking scale (e.g., from 1 to 10) in which prohibited areas (i.e., areas which are defined as area to which the surgical tools are forbidden to 'enter) receive the lowest score (e.g., 1) and preferred areas (i.e., areas which are defined as area in which the surgical tools should be maintained) receive the highest score (e.g., 10).

According to a preferred embodiment, one function $g_i(t)$ is configured to detect tools in the surgical environment and inform the maneuvering function f(t) if they are in preferred areas or in prohibited areas.

According to some embodiments, the movement detection function $g_2(t)$ comprises a communicable database comprising the real-time 3D spatial positions of each of the surgical tools in the surgical environment; means to detect movement of the at least one surgical tool when a change in the 3D spatial positions is received, and means to output instructions to the tracking subsystem to instruct the maneuvering subsystem to direct the endoscope to the moved surgical tool.

According to some embodiments, the organ detection function $g_3(t)$ is configured to detect physiological organs in the surgical environment and to classify the detected organs as prohibited areas or preferred areas. For example, if the operator instructs the system that the specific surgery is kidney surgery, the organ detection function $g_3(t)$ will classify the kidneys (or one kidney, if the surgery is specified to be on a single kidney) as a preferred area and other organs will be classified as prohibited areas. According to another embodiment, the organ detection function is configured to detect organs in the surgical environment and to output instructions to the tracking subsystem to instruct the maneuvering subsystem to direct the endoscope to the detected organs. According to some embodiments, the right tool function is configured to detect surgical tool positioned to right of the endoscope and to output instructions to the tracking subsystem to instruct the maneuvering system to constantly direct the endoscope on the right tool and to track the right tool.

According to another embodiment, the left tool function is configured to detect surgical tool positioned to left of the endoscope and to output instructions to the tracking subsystem to instruct the maneuvering system to constantly direct the endoscope on the left tool and to track the left tool.

According to some embodiments, the collision detection function $g_4(t)$ is configured to detect prohibited areas within the surgical environment so as to prevent collisions between the endoscope and the prohibited areas. For example, if the endoscope is located in a narrow area in which a precise movement of the same is preferred, the collision detection function $g_4(t)$ will detect and classify different areas (e.g., nerves, veins, walls of organs) as prohibited areas. Thus, according to this embodiment, the collision prevention function is configured to define a predetermined distance between the at least one surgical tool and an anatomical element within the surgical environment; and to output instructions to the tracking subsystem to instruct the maneuvering subsystem to direct the endoscope to the surgical tool and the anatomical element within the surgical environment if the distance between the at least one surgical tool and an anatomical element is less than the predetermined distance. According to one embodiment of the present invention the anatomical element is selected from a group consisting of tissue, organ, another surgical tool and any combination thereof.

According to some embodiments, the operator input function $g_5(t)$ is configured to receive an input from the operator. The input can be, for example: an input regarding prohibited areas in the surgical environment, an input regarding allowed areas in the surgical environment, or an input regarding the region of interest and any combination thereof. The operator input function $g_5(t)$ can receive instructions from the operator before or during the surgery, and respond accordingly. According to some embodiments, the operator input function may further comprise a selection algorithm for selection of areas selected from a group consisting of: prohibited areas, allowed areas, regions of interest, and any combination thereof. The selection may be performed via an input device (e.g., a touch screen).

According to some embodiments, the operator input function $g_5(t)$ comprises a communicable database; the communicable database is configured to receive an input from the operator of the system; the input comprising n 3D spatial positions; n is an integer greater than or equal to 2; and to output instructions to the tracking subsystem to instruct the maneuvering subsystem to direct the endoscope to the at least one 3D spatial position received.

According to some embodiments, the prediction function $g_6(t)$ is configured to provide data regarding a surgical environment at a time $t_f > t_0$, wherein to is the present time and $t_f$ is a future time. The prediction function $g_6(t)$ may communicate with a database which stores data regarding the environment of the surgery (e.g., the organs in the environment). This data may be used by the prediction function $g_6(t)$ for the prediction of expected or unexpected events or expected or unexpected objects during the operation. Thus, according to this embodiment, the prediction function $g_6(t)$ comprises a communicable database storing each 3D spatial position of each of surgical tool within the surgical environment, such that each movement of each surgical tool is stored; the prediction function is configured to (a) to predict the future 3D spatial position of each of the surgical tools (or each object); and, (b) to output instructions to the tracking subsystem to instruct the maneuvering subsystem to direct the endoscope to the future 3D spatial position.

According to some embodiments, the past statistical analysis function $g_7(t)$ is configured to provide data regarding the surgical environment or the laparoscopic surgery based on past statistical data stored in a database. The data regarding the surgical environment may be for example: data regarding prohibited areas, data regarding allowed areas, data regarding the region of interest and any combination thereof. Thus, according to this embodiment, the past statistical analysis function $g_6(t)$ comprises a communicable database storing each 3D spatial position of each of surgical tool within the surgical environment, such that each movement of each surgical tool is stored; the past statistical analysis function $g_6(t)$ is configured to (a) perform statistical analysis on the 3D spatial positions of each of the surgical tools in the past; and, (b) to predict the future 3D spatial position of each of the surgical tools; and, (c) to output instructions to the tracking subsystem to instruct the maneuvering subsystem to direct the endoscope to the future 3D spatial position. Thus, according to the past statistical analysis function $g_7(t)$, the past movements of each tool are analyzed and, according to this analysis, a prediction of the tool's next move is provided.

According to another embodiment, the most used tool function $g_8(t)$ comprises a communicable database counting the amount of movement of each surgical tool located within the surgical environment; the most used tool function is configured to output instructions to the tracking subsystem to instruct the maneuvering subsystem to direct the endoscope to constantly position the endoscope to track the movement of the most moved surgical tool. The amount of movement of a tool can be defined as the total number of movements of that tool or the total distance the tool has moved.

According to some embodiments, the right tool function $g_9(t)$ is configured to detect at least one surgical tool in a specified position in relation to the endoscope, preferably positioned to right of the endoscope and to output instructions to the tracking subsystem to instruct the maneuvering subsystem to constantly direct the endoscope to the right tool and to track the same. According to preferred embodiments, the right tool is defined as the tool positioned to the right of the endoscope; according to other embodiments, any tool can be defined as the right tool.

According to another embodiment, the left tool function $g_{10}(t)$ is configured to detect at least one surgical tool in a specified position in relation to the endoscope, preferably positioned to left of the endoscope and to output instructions to the tracking subsystem to instruct the maneuvering subsystem to constantly direct the endoscope to the left tool and to track the same. According to preferred embodiments, the left tool is defined as the tool positioned to the left of the endoscope; according to other embodiments, any tool can be defined as the left tool.

According to another embodiment, the field of view function $g_{11}(t)$ comprises a communicable database comprising n 3D spatial positions; n is an integer greater than or equal to 2; the combination of all of the n 3D spatial positions provides a predetermined field of view; the field of view function is configured to output instructions to the tracking subsystem to instruct the maneuvering subsystem to direct the endoscope to at least one 3D spatial position substantially within the n 3D spatial positions so as to maintain a constant field of view.

According to another embodiment, the preferred volume zone function $g_{12}(t)$ comprises a communicable database comprising n 3D spatial positions; n is an integer greater than or equal to 2; the n 3D spatial positions provide the preferred volume zone; the preferred volume zone function $g_{12}(t)$ is configured to output instructions to the tracking subsystem to instruct the maneuvering subsystem to direct the endoscope to at least one 3D spatial position substantially within the preferred volume zone.

According to another embodiment, the no fly zone function $g_{13}(t)$ comprises a communicable database comprising n 3D spatial positions; n is an integer greater than or equal to 2; the n 3D spatial positions define a predetermined volume within the surgical environment; the no fly zone function $g_{13}(t)$ is configured to output instructions to the tracking subsystem to instruct the maneuvering subsystem to direct the endoscope to at least one 3D spatial position substantially different from all the n 3D spatial positions.

According to some embodiments, the proximity function $g_{14}(t)$ is configured to define a predetermined distance between at least two surgical tools; and to output instructions to the tracking subsystem to instruct the maneuvering subsystem to direct the endoscope to the two surgical tools if the distance between the two surgical tools is less than or if it is greater than the predetermined distance.

According to another embodiment, the proximity function $g_{14}(t)$ is configured to define a predetermined angle between at least three surgical tools; and to output instructions to the tracking subsystem to instruct the maneuvering subsystem to direct the endoscope to the three surgical tools if the angle between the two surgical tools is less than or if it is greater than the predetermined angle.

According to another embodiment, the preferred volume zone function comprises communicable database comprising n 3D spatial positions; n is an integer greater than or equals to 2; the n 3D spatial positions provides the preferred volume zone; the preferred volume zone function is configured to output instructions to the tracking subsystem to instruct the maneuvering system to direct the endoscope to the preferred volume zone.

According to another embodiment, the field of view function comprises a communicable database comprising n 3D spatial positions; n is an integer greater than or equals to 2; the combination of all of the n 3D spatial positions provides a predetermined field of view; the field of view function is configured to output instructions to the tracking subsystem to instruct the maneuvering system to direct the endoscope to at least one 3D spatial position substantially within the n 3D spatial positions so as to maintain a constant field of view.

According to another embodiment, the no fly zone function comprises a communicable database comprising n 3D spatial positions; n is an integer greater than or equals to 2; the n 3D spatial positions define a predetermined volume within the surgical environment; the no fly zone function is configured to output instructions to the tracking subsystem to instruct the maneuvering system to direct the endoscope to at least one 3D spatial position substantially different from all the n 3D spatial positions.

According to another embodiment, the most used tool function comprises a communicable database counting the amount of movement of each surgical tool located within the surgical environment; the most used tool function is configured to output instructions to the tracking subsystem to instruct the maneuvering system to direct the endoscope to constantly position the endoscope to track the movement of the most moved surgical tool.

According to some embodiments, the prediction function $g_6(t)$ is configured to provide data regarding a surgical environment in a time $t_f > t$, wherein t is the present time and $t_f$ is the future time. The prediction function $g_6(t)$ may communicate with a database which stores data regarding the environment of the surgery (e.g., the organs in the environment). This data may be used by the prediction function $g_6(t)$ for the prediction of expected or unexpected events or object during the operation. Thus, according to this embodiment, the prediction function comprises a communicable database storing each 3D spatial position of each of surgical tool within the surgical environment, such that each movement of each surgical tool is stored; the prediction function is configured to (a) to predict the future 3D spatial position of each of the surgical tools; and, (b) to output instructions to the tracking subsystem to instruct the maneuvering system to direct the endoscope to the future 3D spatial position.

According to some embodiments, the past statistical analysis function $g_7(t)$ is configured to provide data regarding the surgical environment or the laparoscopic surgery based on past statistical data stored in a database. The data regarding the surgical environment may be for example: data regarding prohibited areas, data regarding allowed areas, data regarding the region of interest. Thus, according to this embodiment, the past statistical analysis function comprises a communicable database storing each 3D spatial position of each of surgical tool within the surgical environment, such that each movement of each surgical tool is stored; the past statistical analysis function is configured to (a) statistical analyze the 3D spatial positions of each of the surgical tools in the past; and, (b) to predict the future 3D spatial position of each of the surgical tools; and, (c) to output instructions to the tracking subsystem to instruct the maneuvering system to direct the endoscope to the future 3D spatial position. Thus, according to the past statistical analysis function $g_7(t)$, the past movements of each tool are analyzed and according to this analysis a future prediction of the tool's next move is provided.

According to some embodiments, preferred tool function comprises a communicable database, the database stores a preferred tool; the preferred tool function is configured to output instructions to the tracking subsystem to instruct the maneuvering system to constantly direct the endoscope to the preferred tool, such that said endoscope constantly tracks said preferred tool.

Thus, according to the preferred tool function the endoscope constantly tracks the preferred tool, such that the field of view, as seen from the endoscope, is constantly maintained on said preferred tool. It should be noted that the user may define in said preferred tool function to constantly track the tip of said preferred tool or alternatively, the user may define in said preferred tool function to constantly track the body or any location on the preferred tool.

According to some embodiments, the tagged tool function $g_{15}(t)$ comprises means configured to tag at least one surgical tool within the surgical environment and to output instructions to the tracking subsystem to instruct the maneuvering subsystem to constantly direct the endoscope to the tagged surgical tool. Thus, according to the tagged tool function, the endoscope constantly tracks the preferred (i.e., tagged) tool, such that the field of view, as seen from the endoscope, is constantly maintained on the preferred (tagged) tool. It should be noted that the user can define the tagged tool function to constantly track the tip of the preferred (tagged) tool, the body of the preferred (tagged) tool, or any other location on the preferred (tagged) tool.

According to some embodiments, the means are configured to constantly tag at least one surgical tool within the surgical environment.

According to some embodiments, the preferred tool function $g_{16}(t)$ comprises a communicable database. The database stores a preferred tool; and the preferred tool function is configured to output instructions to the tracking subsystem to instruct the maneuvering subsystem to direct the endoscope to the preferred tool.

According to some embodiments, the system further comprises means configured to re-tag the at least one of the surgical tools until a desired tool is selected.

According to some embodiments, the system further comprises means configured to toggle the surgical tools. According to some embodiments, the toggling is performed manually or automatically.

According to different embodiments of the present invention, the weighting functions $\alpha_r(t)$ are time-varying functions (or constants), the value of which is determined by the operator or the output of the instructing functions $g_i(t)$. For example, if a specific function $g_r(t)$ detected an important event or object, its weighting functions $\alpha_r(t)$ may be adjusted in order to elevate the chances that the maneuvering function f(t) will instruct the maneuvering subsystem to move the endoscope towards this important event or object.

According to different embodiments of the present invention, the tracking subsystem may implement various image processing algorithms which may also be algorithms that are well known in the art. The image processing algorithms may be for example: image stabilization algorithms, image improvement algorithms, image compilation algorithms, image enhancement algorithms, image detection algorithms, image classification algorithms, image correlations with the cardiac cycle or the respiratory cycle of the human body, smoke reduction algorithms, vapor reduction algorithms, steam reduction algorithms and any combination thereof. Smoke, vapor and steam reduction algorithms may be needed as it is known that, under certain conditions, smoke, vapor or steam may be emitted by or from the endoscope. The image processing algorithm may also be implemented and used to analyze 2D or 3D representations which may be rendered from the real-time images of the surgical environment.

According to different embodiments, the endoscope may comprise an image acquisition device selected from a group consisting of: a camera, a video camera, an electromagnetic sensor, a computer tomography imaging device, a fluoroscopic imaging device, an ultrasound imaging device, and any combination thereof.

According to some embodiments, the system may also comprise a display configured to provide input or output to the operator regarding the operation of the system. The display may be used to output the acquired real-time images of a surgical environment with augmented reality elements. The display may also be used for the definition of the region of interest by the operator.

According to some embodiments, the endoscope may be controlled be an endoscope controller for performing operations such as: acquiring the real-time images and zooming-in to a predetermined area. For example, the endoscope controller may cause the endoscope to acquire the real-time images in correlation with the cardiac cycle or the respiratory cycle of a human body.

According to different embodiments, the data processor of the present invention may operate a pattern recognition algorithm for assisting the operation of the instructing functions $g_i(t)$. The pattern recognition algorithm may be used as part of the image processing algorithm.

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.).

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.). Reference is made now to FIG. 1, which is a general schematic view of a specific embodiment of a surgical tracking system 100. In this figure are illustrated surgical instruments 17b and 17c and an endoscope 21 which may be maneuvered by means of maneuvering subsystem 19 according to the instructions received from a tracking subsystem operable by computer 15.

According to one embodiment of the present invention as defined in the above, the user may define the field of view function as constantly monitoring at least one of surgical instruments 17b and 17c.

According to this embodiment, the surgical tracking system 100 may also comprise one or more button operated wireless transmitters 12a, which transmit, upon activation, a single code wave 14 through aerial 13 to connected receiver 11 that produces a signal processed by computer 15, thereby directing and modifying the spatial position of endoscope 21 to the region of interest, as defined by the field of view function.

Alternatively, according to the proximity rule, if the distance between the surgical instruments 17b and 17c is smaller than a predetermined distance (as defined by the collision prevention rule), the system alerts the user that any movement of either one of the surgical instruments 17b and 17c that will reduce the distance is a restricted movement.

According to another embodiment of the present invention sound commands are made by the user\s of the system to maneuver either a surgical too (within the surgical environment) or the endoscope (within the surgical environment).

According to another embodiment of the present invention, the input receiving means are configured to convert the input received to a location in which the user\s of the system wishes the tool\endoscope to be positioned at.

According to another embodiment of the present invention, the input can be a touchscreen in wired or wireless communication with said controller, configured to display an image of at least a portion of said surgical environment of said human body and to receive input of said at least one location within said surgical environment of said human body. The input, according to this embodiment, can be pressure (i.e., a touch being made to said touchscreen) applied on said touchscreen.

According to another embodiment of the present invention, the input can be from at least one first camera, in wired or wireless communication with said controller, configured to detect movement of a user's eye. Said eye movement are translated (proportionally) to movement of said tool.

According to another embodiment of the present invention, the input can be from at least one second camera, in wired or wireless communication with said controller, configured to detect movement of at least one body portion of the user; said body portion is selected from a group consisting of hand, elbow, leg. foot, finger and any combination thereof. Said body portion movement are translated (proportionally) to movement of said tool.

According to another embodiment of the present invention, the input can be at least one voice receiving means, in wired or wireless communication with said controller, configured to detect sound. Said sound are translated (proportionally) to movement of said tool It should be emphasized that said tool can be a surgical tool or an endoscope.

According to one embodiment, the location is provided to the system as the desired destination the user\s wishes the tool to be. According to another embodiment, the user\s provide\s the system with an orbit\course\trajectory\path he wishes the tool to be moved.

Thus, according to this embodiment, the system will maneuver the tool according to the path received.

EXAMPLES

Examples are given in order to prove the embodiments claimed in the present invention. The example, which is a clinical test, describes the manner and process of the present invention and set forth the best mode contemplated by the inventors for carrying out the invention, but are not to be construed as limiting the invention.

In the examples below, similar numbers refer to similar parts in all of the figures.

Example 1—Tracking System with Collision Avoidance System

One embodiment of such a rule-based system will comprise the following set of commands:
Detection (denoted by Gd):
Gd1 Tool location detection function
Gd2 Organ (e.g. Liver) detection function
Gd3 Movement (vector) calculation and estimation function
Gd4 Collision probability detection function
Tool Instructions (denoted Gt):
Gt1 Move according to manual command
Gt2 Stop movement
The scenario—manual move command by the surgeon:
Locations Gd1(t) and Gd2(t) are calculated in real time at each time step (from an image or location marker).

Tool movement vector Gd3(t) is calculated from Gd1(t) as the difference between the current location and at least one previous location (probably also taking into account previous movement vectors).

The probability of collision—Gd4(t)—is calculated, for example, from the difference between location Gd1 and location Gd2 (the smaller the distance, the closer the proximity and the higher the probability of collision), from movement vector Gd3(t) indicating a collision, etc.

Tool Instructions $Gt1$ Weight function $\alpha_1(t)=1$ If $Gt1(t)<$a predetermined threshold and 0 otherwise Tool Instructions $Gt2$ Weight function $\alpha_2(t)=1$ If $Gt2(t)>$a predetermined threshold and 0 otherwise Tool Instructions=$\alpha_i(t)*Gt1+\alpha_2(t)*Gt2(t)$;

In reference to FIG. 2, which shows, in a non-limiting manner, an embodiment of a tracking system and collision avoidance system. The system tracks a tool 310 and the liver 320, in order to determine whether a collision between the tool 310 and the liver 320 is possible within the next time step. FIGS. 2a and 2b show how the behavior of the system depends on the distance 330 between the tool 310 and the liver 320, while FIGS. 2c and 2d show how movement of the tool 310 affects the behavior. In FIG. 2a, the distance 330 between the tool 310 and the liver 320 is large enough that a collision is not possible in that time step. Since no collision is possible, no movement of the tool is commanded. In FIG. 2b, the distance 330 between the tool 310 and the liver 320 is small enough that a collision is likely. In the embodiment illustrated, a movement 340 is commanded to move the tool 310 away from the liver 320. In other embodiments, the system prevents movement 350, but does not command movement 340; in such embodiments, the tool 310 will remain close to the liver 320. In yet other embodiments, the system warns/signals the operator that the move is restricted, but does not restrict movement 350 or command movement 340 away from the liver. Such a warning/signaling can be visual or aural, using any of the methods known in the art.

Figure 2A:
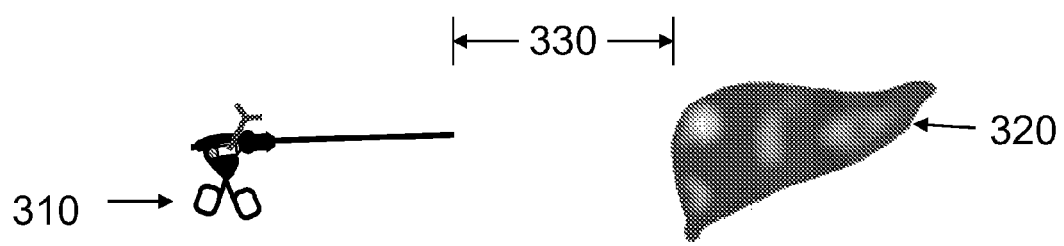
FIG. 2A-D schematically illustrates operation of an embodiment of a tracking system with collision avoidance system.
Figure 2B:
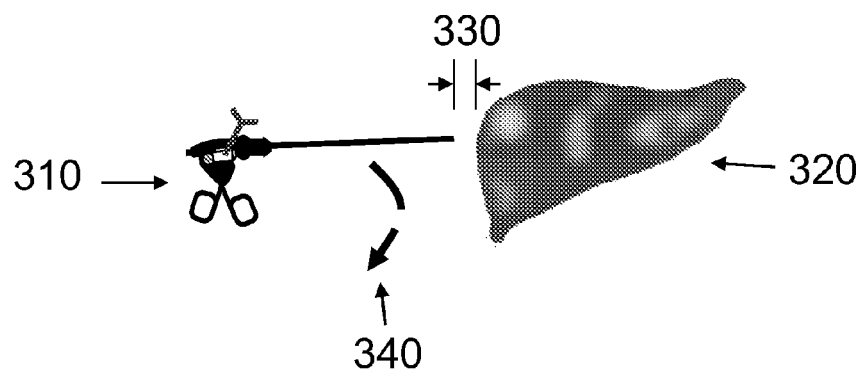
Figure 2C:
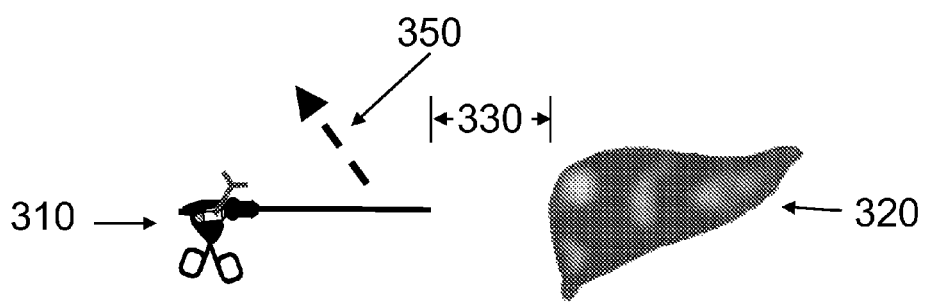
Figure 2D:
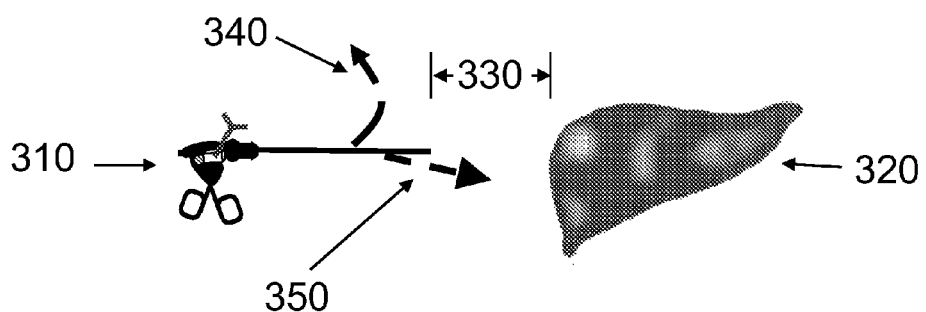

FIGS. 2c and 2d illustrate schematically the effect of the movement of tool 310 on the collision avoidance system. In FIGS. 2c and 2d, the tool 310 is close enough to the liver 320 that a collision between the two is possible. If the system tracked only the positions of the tool 310 and the liver 320, then motion of the tool 310 away from the liver 320 would be commanded. FIG. 2c illustrates the effect of a movement 350 that would increase the distance between tool 310 and liver 320. Since the movement 350 is away from liver 320, no collision is possible in this time step and no movement of the tool 310 is commanded.

In FIG. 2d, tool 310 is the same distance from liver 320 as in FIG. 2c. However, in FIG. 2d, the movement 350 of the tool 310 is toward the liver 320, making a collision between tool 310 and liver 320 possible. In some embodiments, a movement 340 is commanded to move the tool 310 away from the liver 320. In other embodiments, the system prevents movement 350, but does not command movement 340; in this embodiment the tool 310 will remain close to the liver 320. In yet other embodiments, the system warns the operator that move is restricted, but does not restrict movement 350 or command movement 340 away from the liver. Such a warning can be visual or aural, using any of the methods known in the art.

As a non-limiting example, in an operation on the liver, the collision detection function can warn the operator that a collision between a tool and the liver is likely but not prevent the collision. In an operation on the gall bladder, the collision detection function can prevent a collision between the tool and the liver, either by preventing the movement or by commanding a movement redirecting the tool away from the liver, Example 2—Tracking System with Soft Control—Fast Movement when Nothing is Nearby, Slow Movement when Something is Close One embodiment of such rule-based system comprises the following set of commands:
Detection (denoted by Gd):
Main Tool location detection function (denoted by GdM);
Gd-tool1-K—Tool location detection function;
Gd-organ2-L—Organ (e.g. Liver) detection function;
Gd3 Main Tool Movement (vector) calculation and estimation function;
Gd4 Proximity probability detection function;
Tool Instructions (denoted Gt):
Gt1 Movement vector (direction and speed) according to manual command
The scenario—manual move command by the surgeon:
Locations GdM(t), Gd-tool1-K(t) and Gd-organ2-L(t) are calculated in real time at each time step (from image or location marker).

Main Tool Movement Vector Gd3(t) is calculated per GdM (t) as the difference between the current location and at least one previous location (probably also taking into account previous movement vectors)

The proximity of the main tool to other tools—Gd4(t)—is calculated, for example, as the smallest of the differences between the main tool location and the other tools' locations.

Tool Instructions Gt1 Weight function $\alpha_f(t)$ is proportional to tool proximity function Gd4(t), the closer the tool the slower the movement so that, for example $\alpha_2(t)=Gd4/\text{maximum}(Gd4)$ or $\alpha_2(t)=\log(Gd4/\text{maximum}(Gd4))$ where maximum(Gd4) is the maximum distance which is likely to result in a collision given the distances, the speed of the tool and the movement vector.

Tool Instructions=$\alpha_1(t)*Gt1$.

Example 3—Tracking System with No-Fly Rule/Function

In reference to FIG. 3, which shows, in a non-limiting manner, an embodiment of a tracking system with no-fly rule. The system tracks a tool 310 with respect to a no-fly zone (460), in order to determine whether the tool will enter the no-fly zone (460) within the next time step. In this example, the no-fly zone 460 surrounds the liver.

Figure 3A:
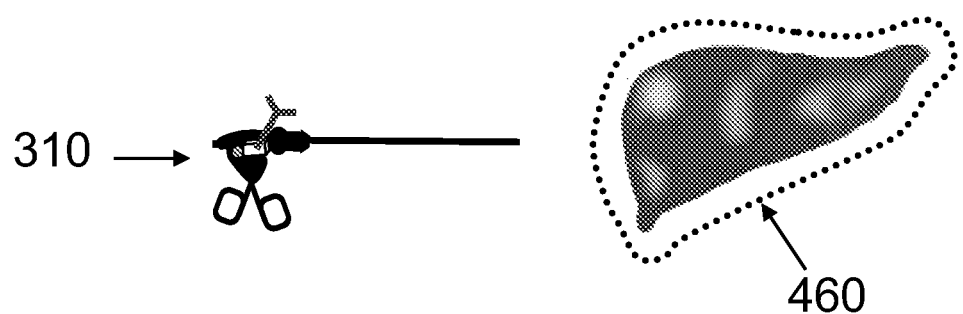
FIG. 3A-D schematically illustrates operation of an embodiment of a tracking system with no fly zone rule/function.
Figure 3B:
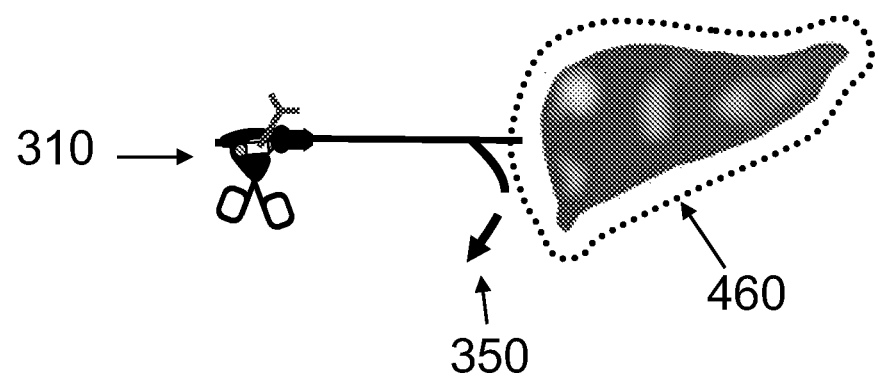
Figure 3C:
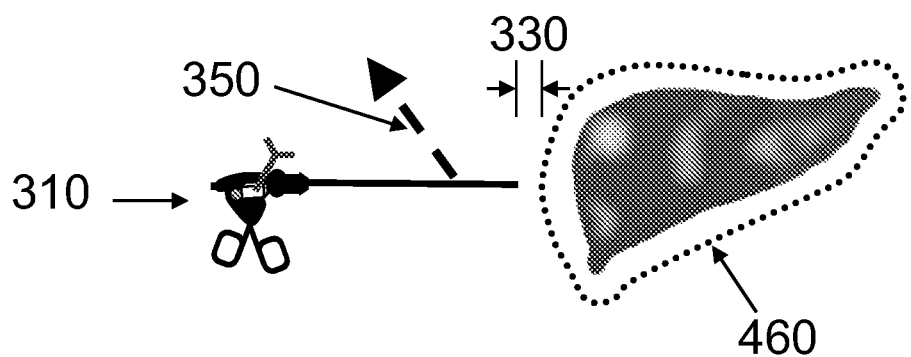
Figure 3D:
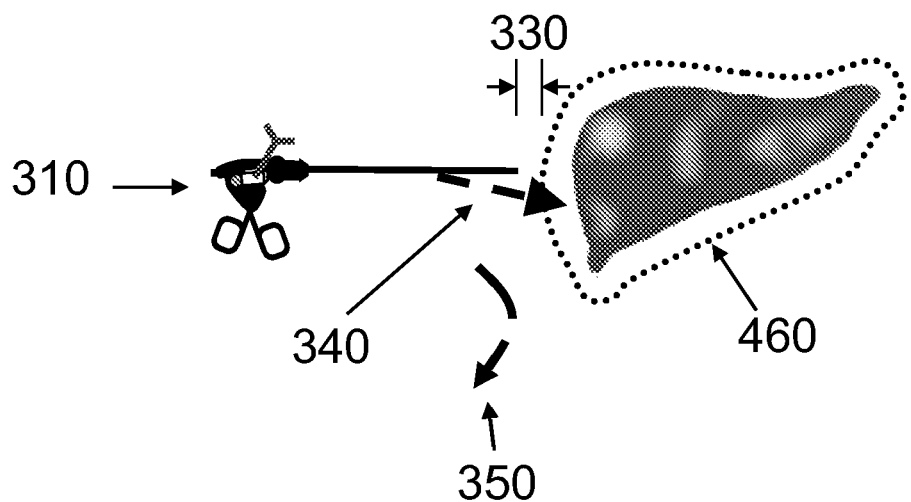

FIGS. 3a and 3b show how the behavior of the system depends on the location of the tool tip with respect to the no-fly zone, while FIGS. 3c and 3d show how movement of the tool affects the behavior.

In FIG. 3a, the tool 310 is outside the no-fly zone rule/function 460 and no movement of the tool is commanded. In FIG. 3b, the tool 310 is inside the no-fly zone 460.

The no-fly zone rule/function performs as follows:

In the embodiment illustrated, a movement 350 is commanded to move the tool 310 away from the no-fly zone 460. In other embodiments, the system prevents movement further into the no-fly zone (refers as movement 340, see FIG. 3c), but does not command movement 340; in such embodiments, the tool 310 will remain close to the no-fly zone 460.

In yet other embodiments, the system warns/signals the operator that the move is restricted, but does not restrict movement further into the no-fly zone or command movement 340 away from the no-fly zone 460. Such a warning/signaling can be visual or aural, using any of the methods known in the art.

FIGS. 3c and 3d illustrate schematically the effect of the tool's movement on operation of the no-fly zone rule/function. In FIGS. 3c and 3d, the tool 310 is close enough to the no-fly zone 460 (distance 330 is small enough) that it is possible for the tool to enter the no-fly zone during the next time step. FIG. 3c illustrates the effect of a movement 340 that would increase the distance between tool 310 and no-fly zone 460. Since the movement 340 is away from no-fly zone 460, no collision is possible in this time step and no movement of the tool 310 is commanded.

In FIG. 3d, tool 310 is the same distance from no-fly zone 460 as in FIG. 3c. However, in FIG. 3d, the movement 340 of the tool is toward no-fly zone 460, making it possible for tool 310 to enter no-fly zone 460. In the embodiment illustrated, a movement 350 is commanded to move the tool 310 away from the no-fly zone 460. In other embodiments, the system prevents movement 340, but does not command movement 350; in such embodiments, the tool 310 will remain close to the no-fly zone 460. In yet other embodiments, the system warns/signals the operator that the move is restricted, but does not restrict movement 340 or command movement 350 away from the no-fly zone rule/function 460. Such a warning/signaling can be visual or aural, using any of the methods known in the art.

Example 4—Tracking System with Preferred Volume Zone Rule/Function

In reference to FIG. 4, which shows, in a non-limiting manner, an embodiment of a tracking system with a preferred volume zone function/rule.

The system tracks a tool 310 with respect to a preferred volume zone (570), in order to determine whether the tool will leave the preferred volume (570) within the next time step.

Figure 4A:
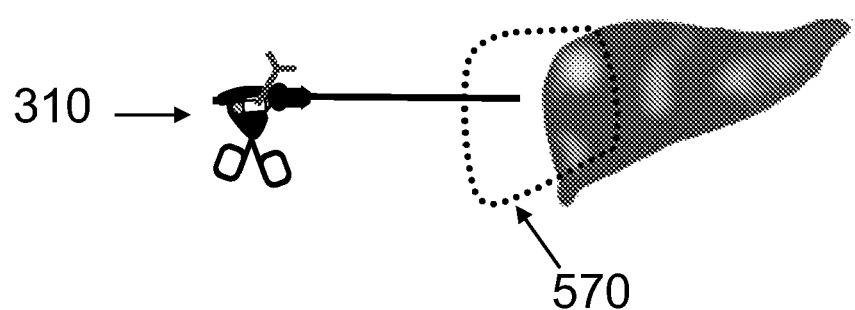
FIG. 4A-D schematically illustrates operation of an embodiment of a tracking system with preferred volume zone rule/function.
Figure 4B:
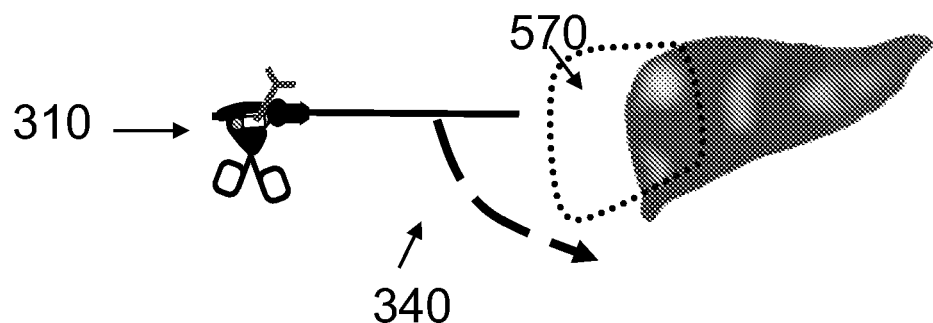

In this example, the preferred volume zone 570 extends over the right lobe of the liver. FIGS. 4a and 4b show how the behavior of the system depends on the location of the tool tip with respect to the preferred volume zone 570, while FIGS. 4c and 4d show how movement of the tool affects the behavior (i.e., the preferred volume zone rule/function).

In FIG. 4a, the tool 310 is inside the preferred volume zone 570 and no movement of the tool is commanded. In FIG. 4b, the tool 310 is outside the preferred volume zone 570.

In the embodiment illustrated, a movement 340 is commanded to move the tool 310 away from the preferred volume zone 570. In other embodiments, the system prevents movement 340; in such embodiments, the tool 310 will remain close to the preferred volume zone 570. In yet other embodiments, the system warns/signals the operator that the move 340 is restricted. Such a warning/signaling can be visual or aural, using any of the methods known in the art.

Figure 4C:
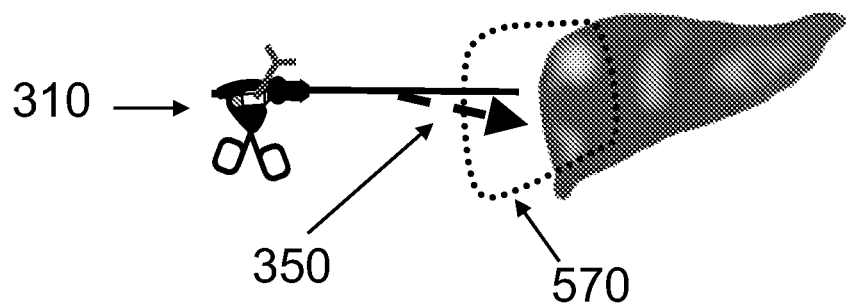
Figure 4D:
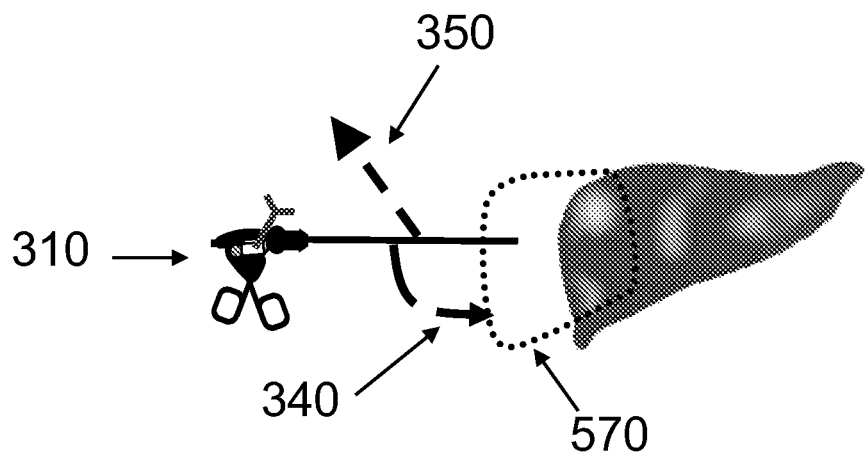

FIGS. 4c and 4d illustrate schematically the effect of the tool's movement on operation of the preferred volume rule/function. In FIGS. 4c and 4d, the tool 310 is close enough to the edge of preferred volume zone 570 that it is possible for the tool to leave the preferred volume zone during the next time step.

FIG. 4c illustrates the effect of a movement 350 that would take the tool 310 deeper into preferred volume zone 570. Since the movement 350 is into preferred volume 570, said movement is an allowed movement.

In FIG. 4d, the movement 350 of the tool is out of the preferred volume 570, making it possible for tool 310 to leave preferred volume 570.

According to one embodiment illustrated, a movement 340 is commanded to move the tool 310 into the preferred volume zone 570. In other embodiments, the system prevents movement 350, but does not command movement 340; in such embodiments, the tool 310 will remain close to the preferred volume zone 570. In yet other embodiments, the system warns/signals the operator that the move is restricted, but does not restrict movement 350 or command movement 340 away from the preferred volume zone 570. Such a warning/signaling can be visual or aural, using any of the methods known in the art.

Example 5—Organ/Tool Detection Function

Figure 5:
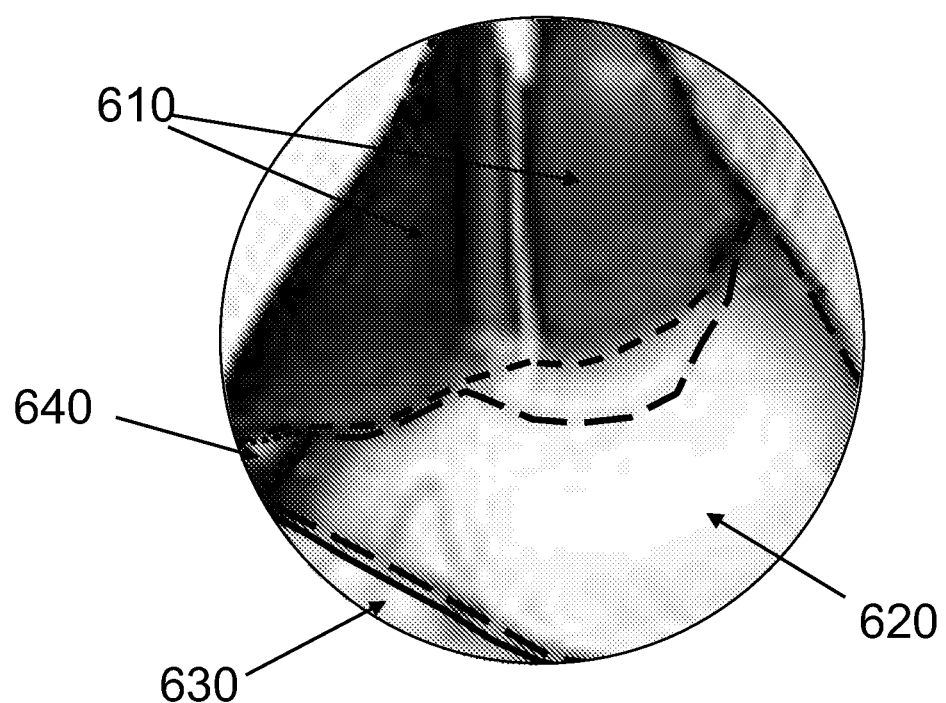
FIG. 5 schematically illustrates operation of an embodiment of the organ detection function/rule.

In reference to FIG. 5, which shows, in a non-limiting manner, an embodiment of an organ detection system (however, it should be noted that the same is provided for detection of tools, instead of organs).

For each organ, the 3D spatial positions of the organs stored in a database. In FIG. 5, the perimeter of each organ is marked, to indicate the edge of the volume of 3D spatial locations stored in the database.

In FIG. 5, the liver 610 is labeled with a dashed line. The stomach 620 is labeled with a long-dashed line, the intestine 630 with a solid line and the gall bladder 640 is labeled with a dotted line.

In some embodiments, a label or tag visible to the operator is also presented. Any method of displaying identifying markers known in the art can be used. For non-limiting example, in an enhanced display, colored or patterned markers can indicate the locations of the organs, with the marker either indicating the perimeter of the organ or the area of the display in which it appears.

Example 6—Tool Detection Function

Figure 6:
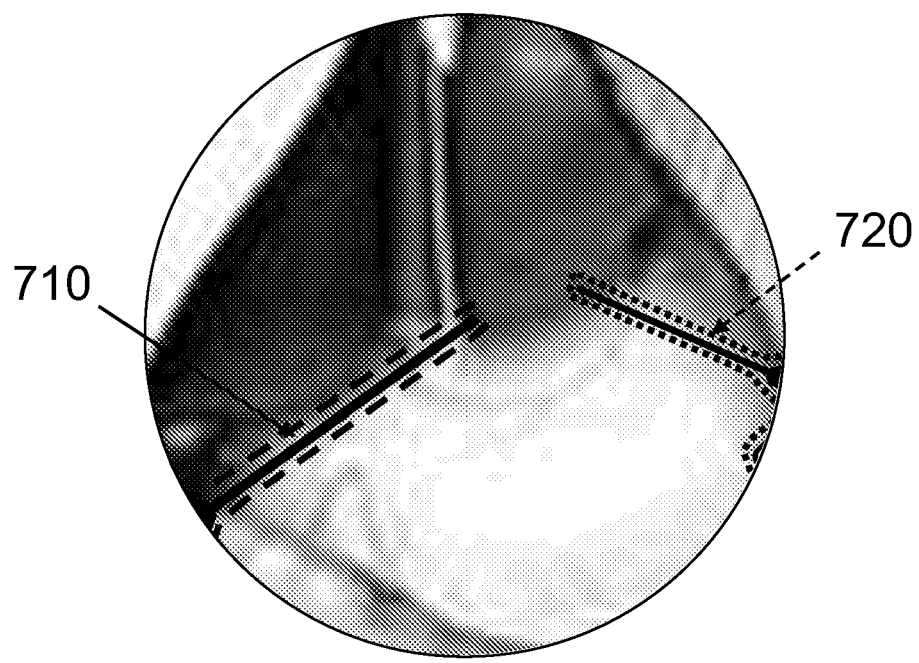
FIG. 6 schematically illustrates operation of an embodiment of the tool detection function/rule.

In reference to FIG. 6, which shows, in a non-limiting manner, an embodiment of a tool detection function. For each tool, the 3D spatial positions of the tools stored in a database. In FIG. 6, the perimeter of each tool is marked, to indicate the edge of the volume of 3D spatial locations stored in the database. In FIG. 6, the left tool is labeled with a dashed line 710 while the right tool is labeled with a dotted line 720.

In some embodiments, a label or tag visible to the operator is also presented. Any method of displaying identifying markers known in the art can be used. For non-limiting example, in an enhanced display, colored or patterned markers can indicate the locations of the tools, with the marker either indicating the perimeter of the tool or the area of the display in which it appears.

Example 7—Movement Detection Function/Rule

Figure 7A:
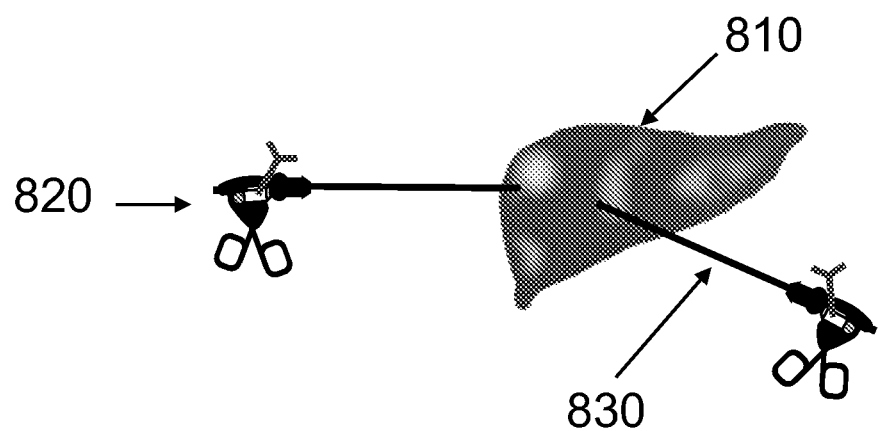
FIG. 7A-B schematically illustrates operation of an embodiment of the movement detection function/rule.
Figure 7B:
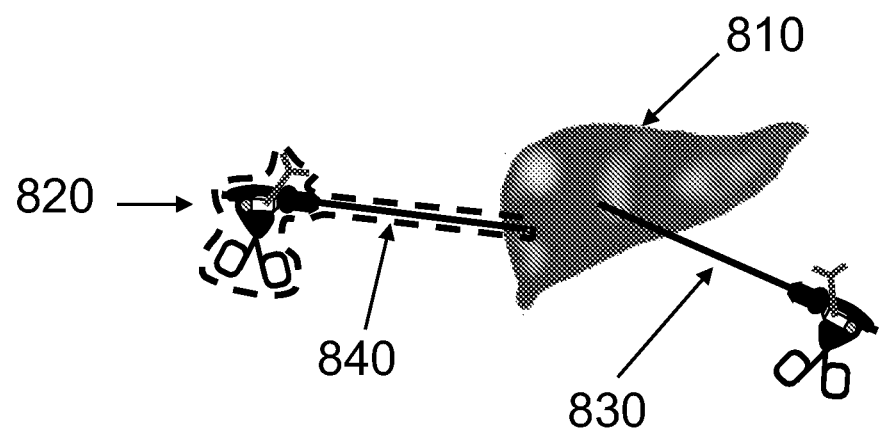

In reference to FIG. 7, which shows, in a non-limiting manner, an embodiment of a movement detection function/rule. FIG. 7a schematically illustrates a liver 810, a left tool 820 and a right tool 830 at a time t. FIG. 7b schematically illustrates the liver 810, left tool 820 and right tool 830 at a later time t+Δt, where Δt is a small time interval. In this example, the left tool 820 has moved downward (towards the direction of liver 810) in the time interval Δt.

The system has detected movement of left tool 820 and labels it. This is illustrated schematically in FIG. 7B by a dashed line 840 around left tool 820.

Example 8—Prediction Function

In reference to FIG. 8, which shows, in a non-limiting manner, an embodiment of the above discussed prediction function.

Figure 8A:
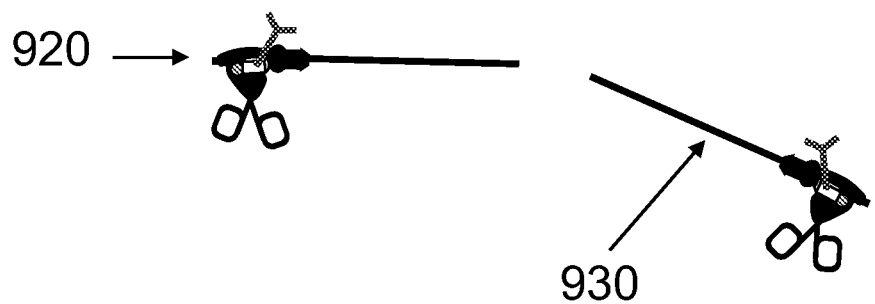
FIG. 8A-D schematically illustrates operation of an embodiment of the prediction function/rule.

FIG. 8a shows a left tool 920 and a right tool 930 at a time t.

Figure 8B:
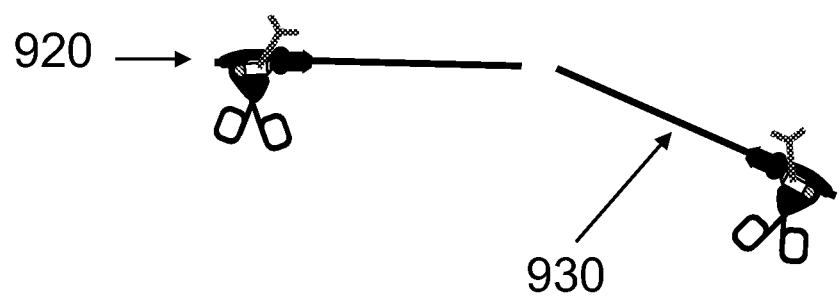
Figure 8C:
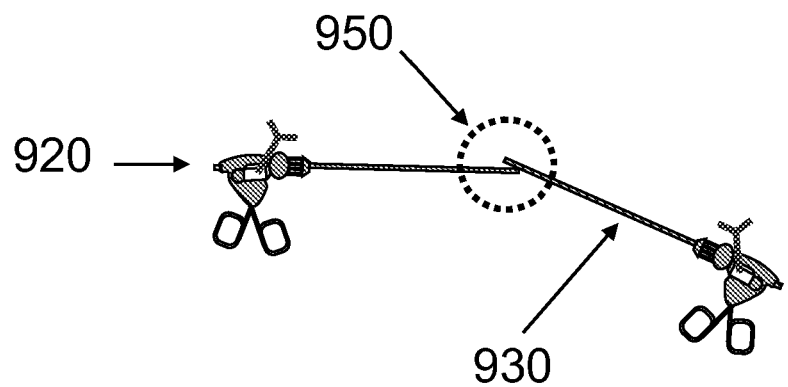
Figure 8D:
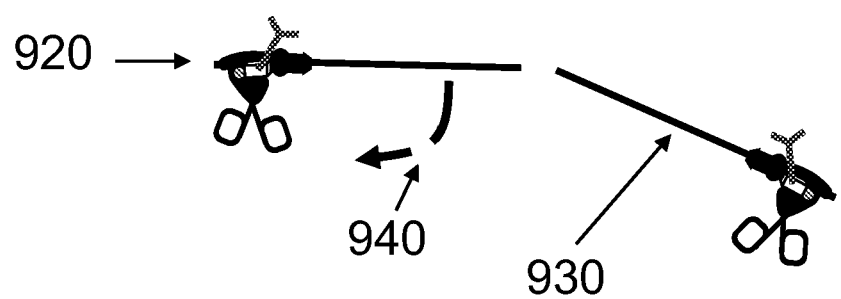

FIG. 8b shows the same tools at a later time t+Δt, where Δt is a small time interval. Left tool 920 is moving to the right and downward, while right tool 930 is moving to the left and upward. If the motion continues (shown by the dashed line in FIG. 8c), then by the end of the next time interval, in other words, at some time between time t+Δt and time t+2a Δt, the tools will collide, as shown by tool tips within the dotted circle 950 in FIG. 8c.

In this embodiment, the system automatically prevents predicted collisions and, in this example, the system applies a motion 940 to redirect left tool 920 so as to prevent the collision.

In other embodiments, the system warns/signals the operator that a collision is likely to occur, but does not alter the movement of any tool. Such a warning/signaling can be visual or aural, using any of the methods known in the art.

In other embodiments, the prediction function can be enabled to, for non-limiting example, alter the field of view to follow the predicted movement of a tool or of an organ, to warn of (or prevent) predicted motion into a no-fly zone, to warn of (or prevent) predicted motion out of a preferred zone.

Example 9—Right Tool Function/Rule

Figure 9:
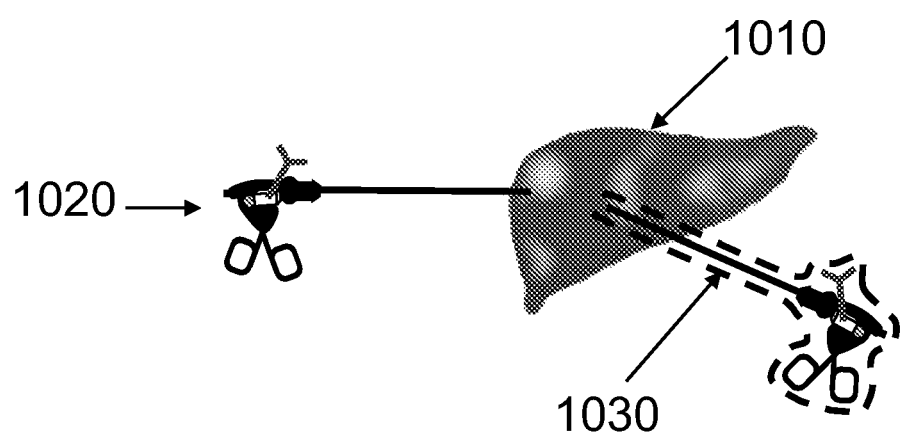
FIG. 9 schematically illustrates operation of an embodiment of the right tool function/rule.

In reference to FIG. 9, which shows, in a non-limiting manner, an embodiment of a right tool function. FIG. 9 schematically illustrates a liver 1010, a left tool 1020 and a right tool 1030. The right tool, illustrated schematically by the dashed line 1040, is labeled and its 3D spacial location is constantly and real-time stored in a database. Now, according to the right tool function/rule the endoscope constantly tracks the right tool.

It should be pointed out that the same rule/function applies for the left tool (the left tool function/rule).

Example 10—Field of View Function/Rule

In reference to FIG. 10, which shows, in a non-limiting manner, an embodiment of a field of view function/rule.

Figure 10A:
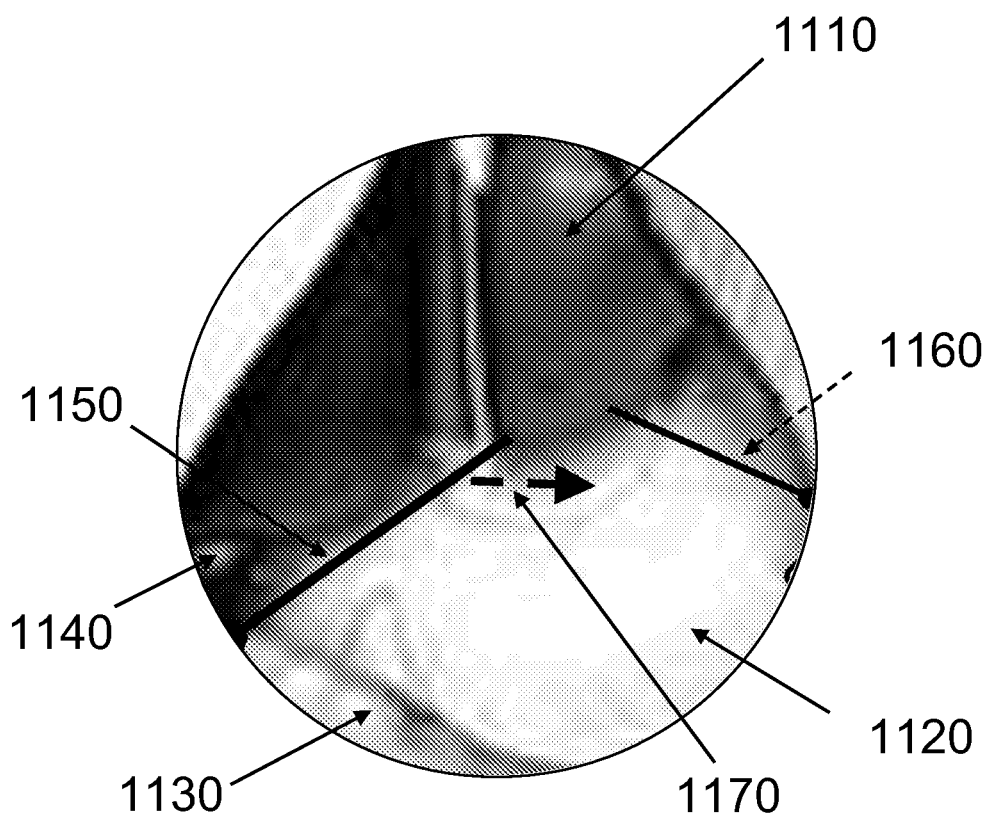
FIG. 10A-B schematically illustrates operation of an embodiment of the field of view function/rule.

FIG. 10a schematically illustrates a field of view of the abdomen at a time t. In the field of view are the liver 1110, stomach 1120, intestines 1130 and gall bladder 1140.

The gall bladder is nearly completely visible at the left of the field of view. Two tools are also in the field of view, with their tips in proximity with the liver. These are left tool 1150 and right tool 1160. In this example, the field of view function/rule tracks left tool 1150. In this example, left tool 1150 is moving to the right, as indicated by arrow 1170.

Figure 10B:
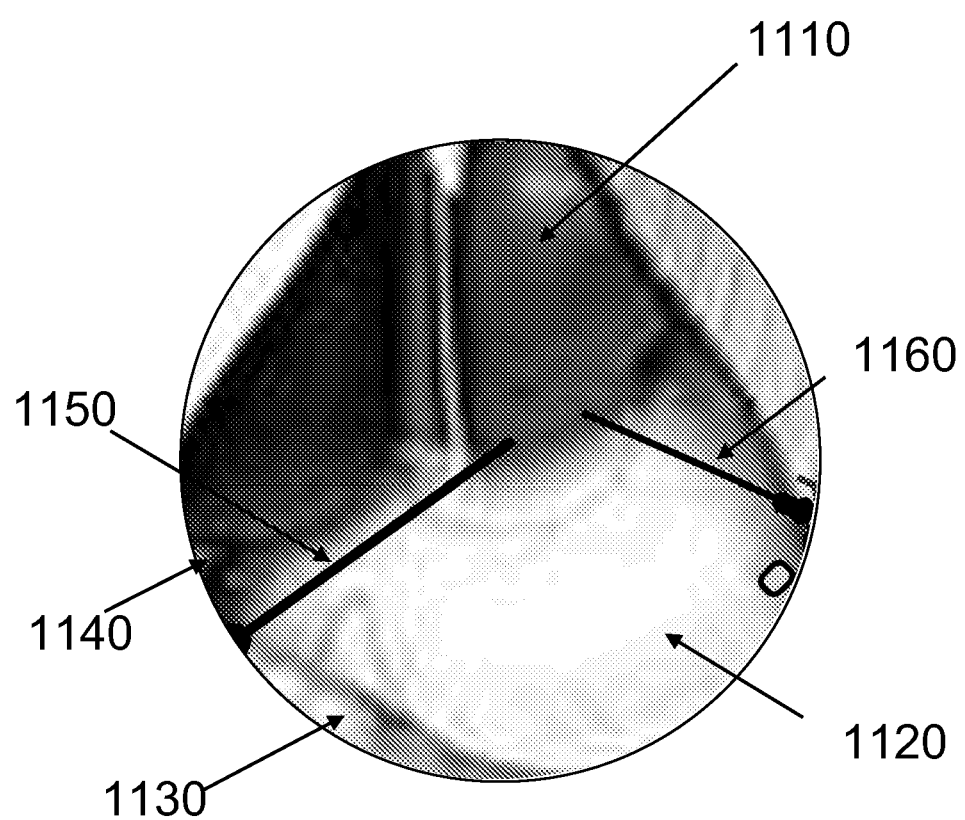

FIG. 10b shows the field of view at time t+Δt. The field of view has moved to the right so that the tip of left tool 1150 is still nearly at the center of the field of view. It can be seen that much less of gall bladder 1140 is visible, while more of right tool 1160 has entered the field of view.

The field of view function/rule can be set to follow a selected tool, as in this example, or to keep a selected organ in the center of the field of view. It can also be set to keep a particular set of tools in the field of view, zooming in or out as necessary to prevent any of the chosen tools from being outside the field of view.

Alternatively, the field of view function/rule defines n 3D spatial positions; n is an integer greater than or equal to 2; the combination of all of said n 3D spatial positions provides a predetermined field of view.

Each movement of the endoscope or the surgical tool within said n 3D spatial positions is an allowed movement and any movement of the endoscope or the surgical tool outside said n 3D spatial positions is a restricted movement.

Alternatively, said the field of view function/rule defines n 3D spatial positions; n is an integer greater than or equal to 2; the combination of all of said n 3D spatial positions provides a predetermined field of view.

According to the field of view function/rule, the endoscope is relocated if movement has been detected by said detection means, such that said field of view is maintained.

Example 11—Tagged Tool Function/Rule (or Alternatively the Preferred Tool Rule)

Figure 11:
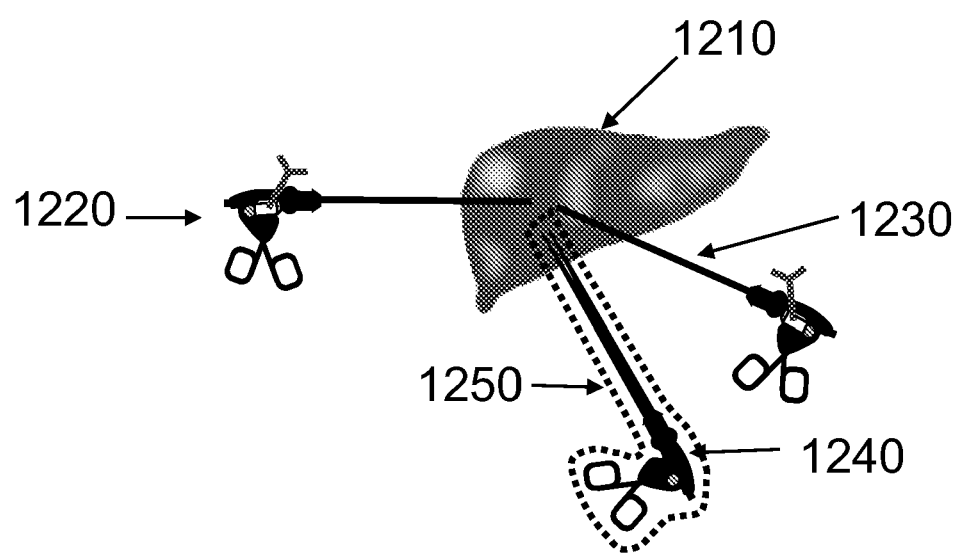
FIG. 11 schematically illustrates operation of an embodiment of the tagged tool function/rule.

In reference to FIG. 11, which shows, in a non-limiting manner, an embodiment of a tagged tool function/rule.

FIG. 11 shows three tools (1220, 1230 and 1240) in proximity to the organ of interest, in this example, the liver 1210.

The tool most of interest to the surgeon, at this point during the operation, is tool 1240. Tool 1240 has been tagged (dotted line 1250); the 3D spacial location of tool 1240 is constantly stored in a database and this spacial location has been labeled as one of interest.

The system can use this tagging for many purposes, including, but not limited to, keeping tool 1240 in the center of the field of view, predicting its future motion, keeping it from colliding with other tools or keeping other tools from colliding with it, instructing the endoscope to constantly monitor and track said tagged tool 1250 and so on.

It should be noted that in the preferred tool rule, the system tags one of the tools and performs as in the tagged tool rule/function.

Example 12—Proximity Function/Rule

In reference to FIG. 12, which shows, in a non-limiting manner, an embodiment of a proximity function/rule.

Figure 12A:
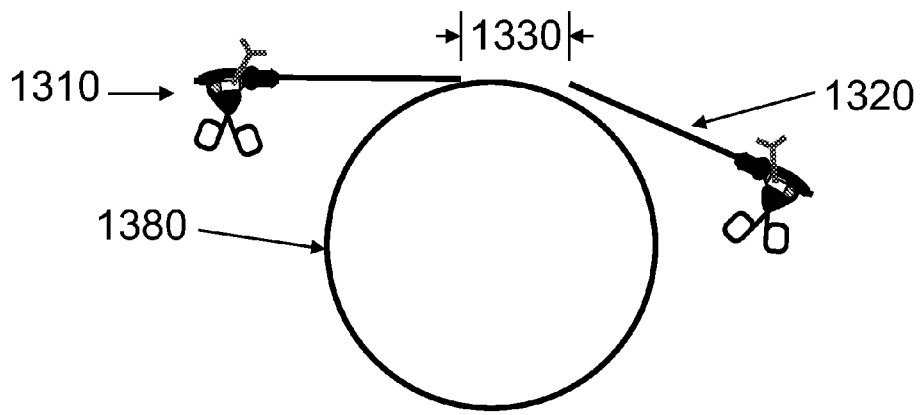
FIG. 12A-C schematically illustrates operation of an embodiment of the proximity function/rule.

FIG. 12*a* schematically illustrates two tools (1310 and 1320) separated by a distance 1330 which is greater than a predefined proximity distance. Since tool 1310 is not within proximity of tool 1320, the field of view (1380) does not move.

Figure 12B:
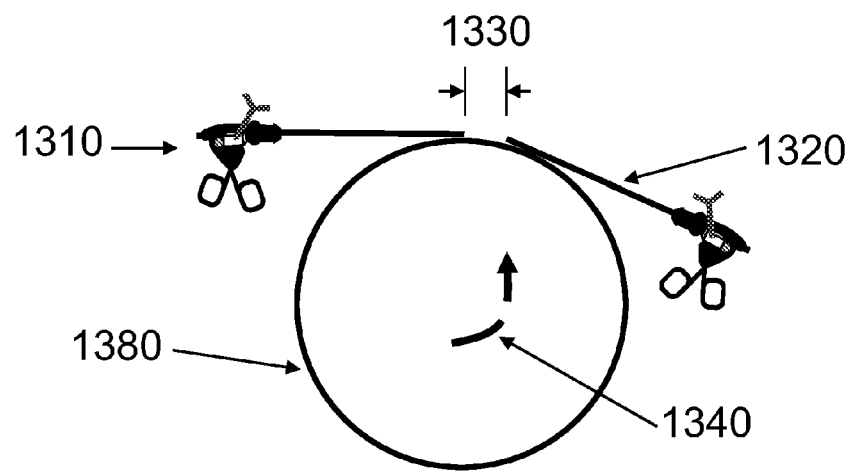

FIG. 12*b* schematically illustrates two tools (1310 and 1320) separated by a distance 1330 which is less than a predefined proximity distance.

Figure 12C:
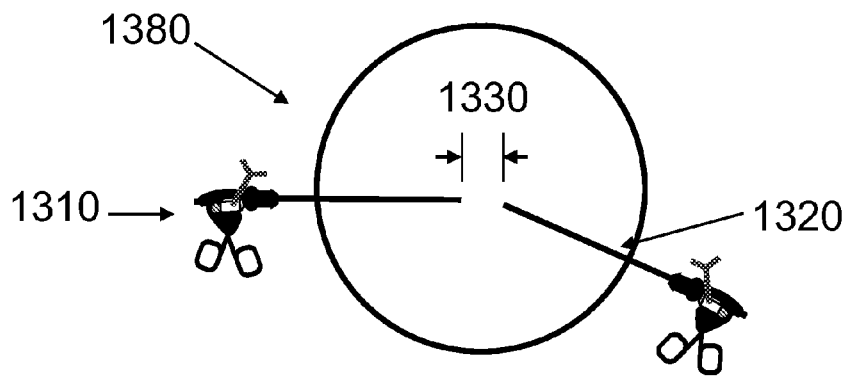

Since tool 1310 is within proximity of tool 1320, the field of view 1380 moves upward, illustrated schematically by arrow 1340, until the tips of tool 1310 and tool 1320 are in the center of field of view 1380 (FIG. 12*c*).

Alternatively the once the distance 1330 between the two tool 1320 and 1310 is smaller than a predetermined distance, the system alerts the user of said proximity (which might lead to a collision between the two tools). Alternatively, the system moves one of the tools away from the other one.

Example 13—Operator Input Function/Rule

In reference to FIG. 13, which shows, in a non-limiting manner, an embodiment of an operator input function/rule. According to this embodiment, input is received from the operator.

In a first example of the operator input function, the input received from the operator is which tool to track.

Figure 13A:
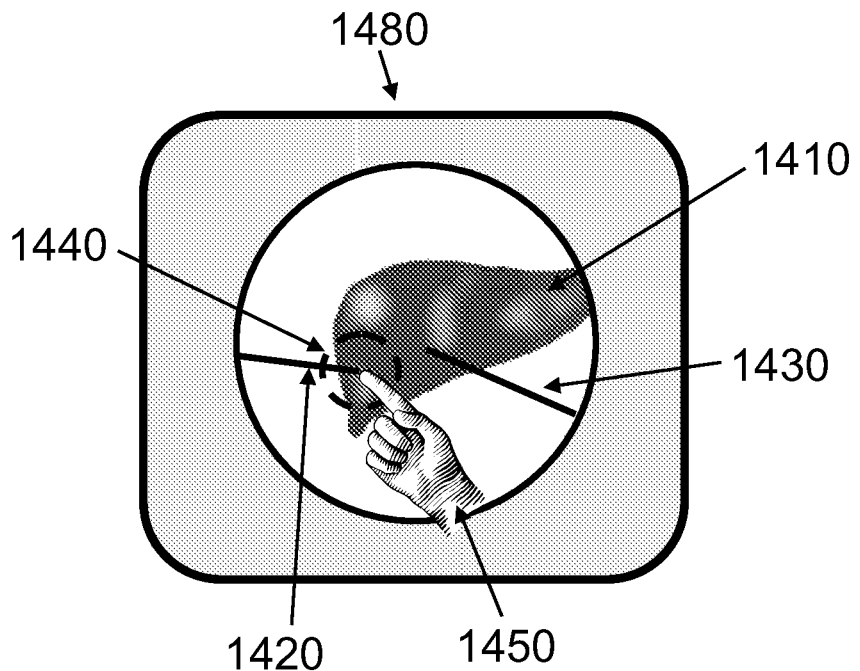
FIGS. 13A-13G schematically illustrate operation of an embodiment of the operator input function/rule.

FIG. 13*a* schematically illustrates an endoscope with field of view 1480 showing a liver 1410 and two tools 1420 and 1430. Operator 1450 first selects the tip of the left tool as the region of interest, preferably by touching the tool tip on the screen, causing the system to tag (1440) the tip of the left tool.

Figure 13B:
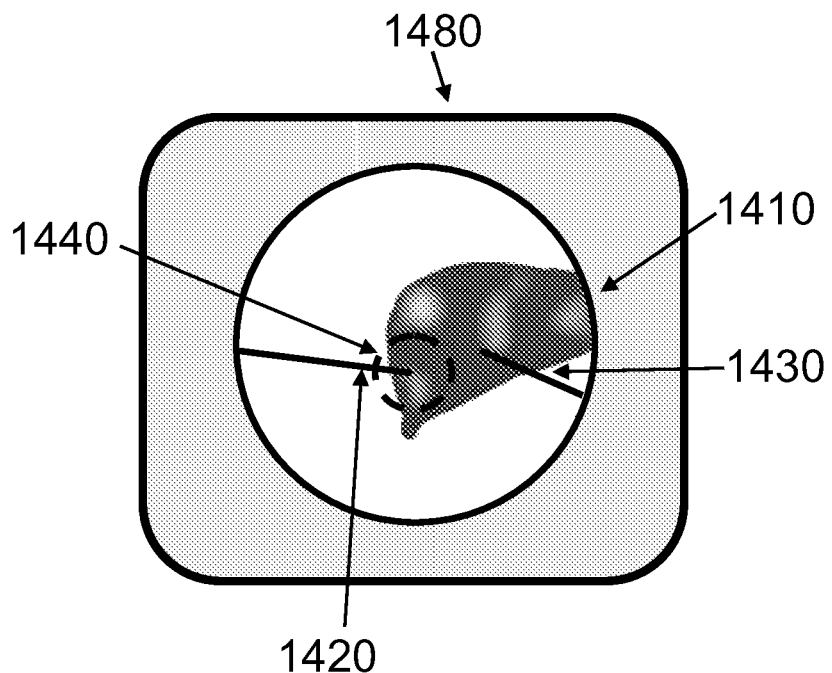

As illustrated in FIG. 13*b*, the system then directs and modifies the spatial position of the endoscope so that the tagged tool tip 1440 is in the center of the field of view 1480.

A second example of the operator input function/rule is the following:

If a tool has been moved close enough to an organ in the surgical environment, according to the proximity rule or the collision prevention rule, the system will, according to one embodiment, prevent the movement of that surgical tool.

According to one embodiment of the present invention, once the surgical tool has been stopped, any movement of the tool in a direction toward the organ is interpreted as input from the operator to continue the movement of that surgical tool in that direction.

Thus, according to this embodiment, the operator input function/rule receives input from the operator (i.e., physician) to continue the movement of the surgical tool (even though it is "against" the collision prevention rule). The input is simply in the form of the continued movement of the surgical tool (after the alert of the system or after the movement prevention by the system).

In a third example of the operator input function, the input received from the operator is the location of the center of the field of view.

Figure 13C:
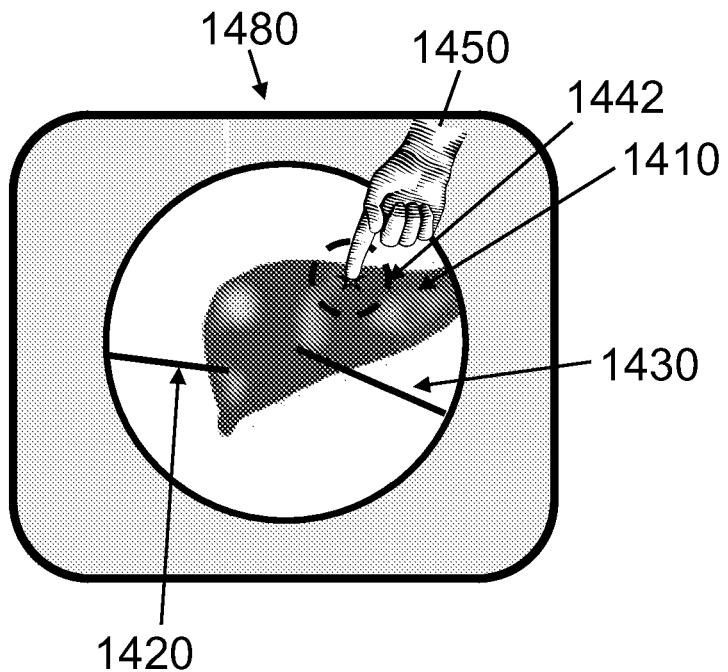

FIG. 13*c* schematically illustrates an endoscope with field of view 1480 showing a liver 1410 and two tools 1420 and 1430. Operator 1450 selects a position (grey star) near the top of the left lobe of the liver as the center of the field of view, preferably by touching the liver on the screen, causing the system to tag (1442, dashed circle) the selected position.

Figure 13D:
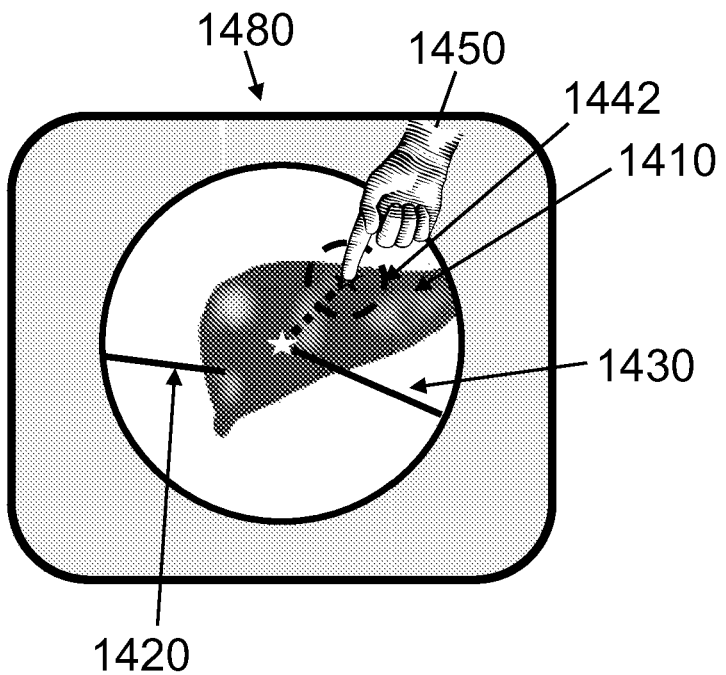

In this example, the operator 1450 has touched the screen but has not indicated a desired path for the endoscope to follow, for example, by drawing a finger across the screen. Therefore, the path followed by the endoscope will be determined automatically by the system. An exemplary path is shown in FIG. 13*d*, which can modify the spatial position of the endoscope so that the center of the field of view (white star) will be moved (dashed line) from its present position to the selected position (grey star).

Many other paths are possible; the actual path will depend on many factors, including, but not limited to, the rules given herein and the characteristics of the maneuvering system.

Figure 13E:
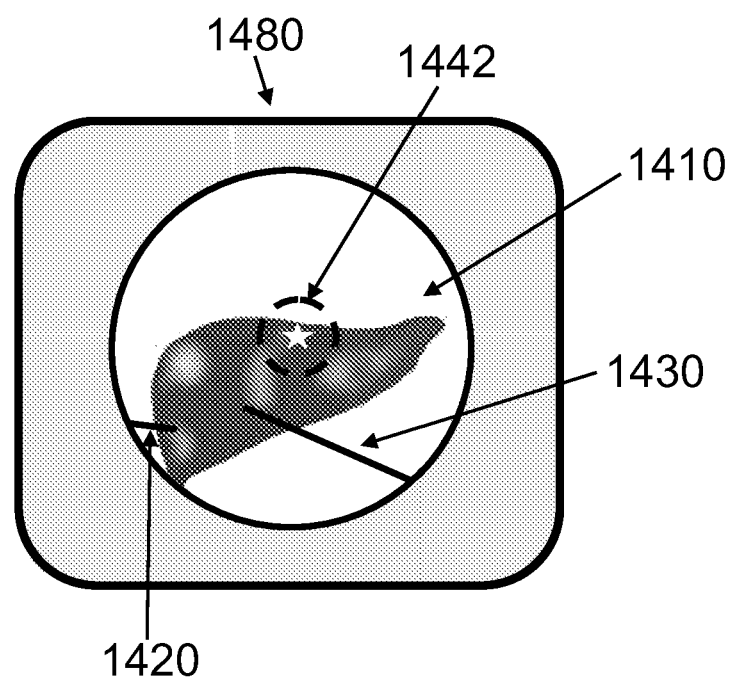

As illustrated in FIG. 13*e*, the system then directs and modifies the spatial position along the path of the endoscope so that the selected position (grey star) which has been tagged (1442, dashed circle), is in the center of the field of view 1480.

In this case, it should be noted that the tools are not attached to the endoscope; moving the endoscope does not affect the position of the tools.

In a fourth example of the operator input function, the input received from the operator is the path to be followed by the endosocpe.

Figure 13F:
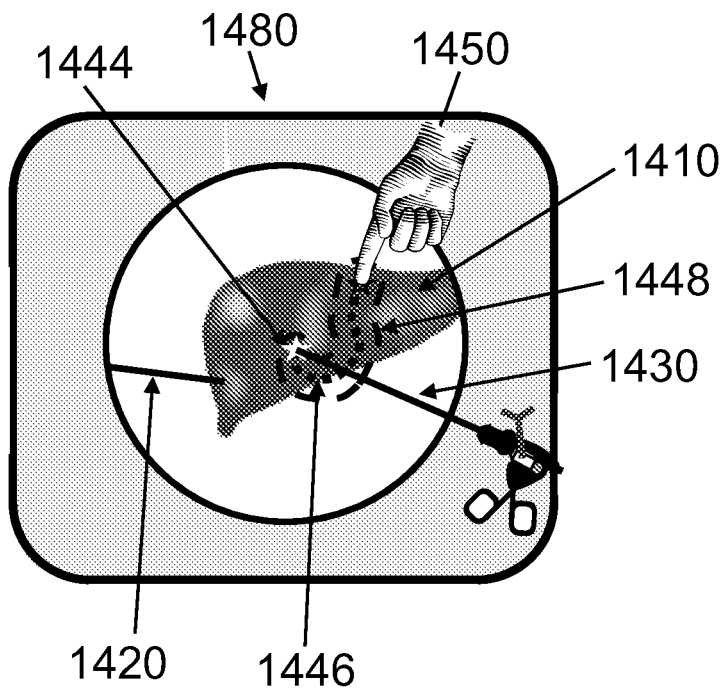

FIG. 13*f* schematically illustrates an endoscope with field of view 1480 showing a liver 1410 and two tools 1420 and 1430. Operator 1450 selects a path 1446 for the center of the field of view (white star) to follow as it moves from its current location 1444 to a position near the top of the left lobe of the liver, preferably by tracing the path 1446 on the screen, causing the system to tag (1448) the path.

Figure 13G:
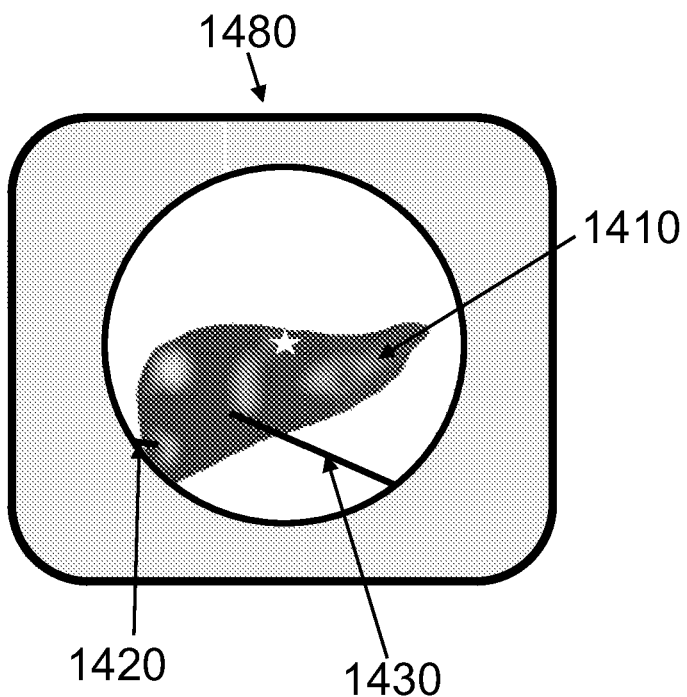

As illustrated in FIG. 13*g*, the system then directs and modifies the spatial position of the tool so that, after the tool follows the tagged path 1446, the center of the field of view is at the selected position.

In this example, the locations of the tools are unaffected by the movement of the endoscope since the tools are not attached to the endoscope. If a tool were attached to the endoscope, then, in addition to the center of the field of view being moved, the tool tip would move along with the endoscope.

Example 14—Constant Field of View Rule/Function

In reference to FIGS. 14*a-d*, which shows, in a non-limiting manner, an embodiment of a tracking system with a constant field of view rule/function.

In many endoscopic systems, the tip lens in the camera optics is not at a right angle to the sides of the endoscope. Conventionally, the tip lens angle is described relative to the right angle, so that a tip lens at right angles to the sides of the endoscope is described as having an angle of 0. Typically, angled endoscope tip lenses have an angle of 30° or 45°. This tip lens angle affects the image seen during zooming. FIG. 14 illustrates, in an out-of-scale manner, for a conventional system, the effect of zooming in the field of view in an endoscope with tip lens set straight in the end (FIGS. 14*a* and 14*b*) vs. the effect of zooming in the field of view in an endoscope with angled tip lens (FIGS. 14*c* and 14*d*).

Figure 14A:
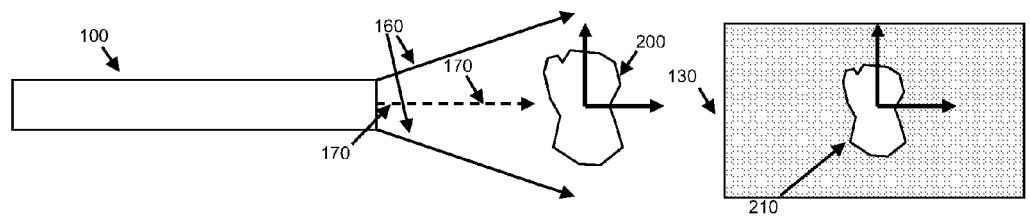
FIGS. 14A-D schematically illustrate an embodiment of a tracking system with a constant field of view rule/function.
Figure 14B:
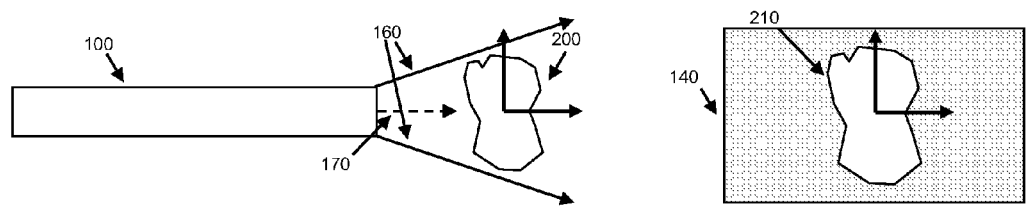
Figure 14C:
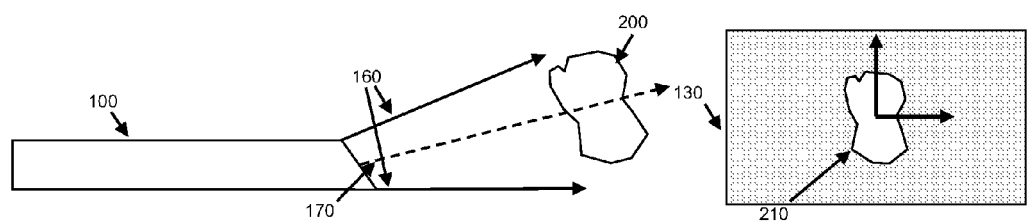
Figure 14D:
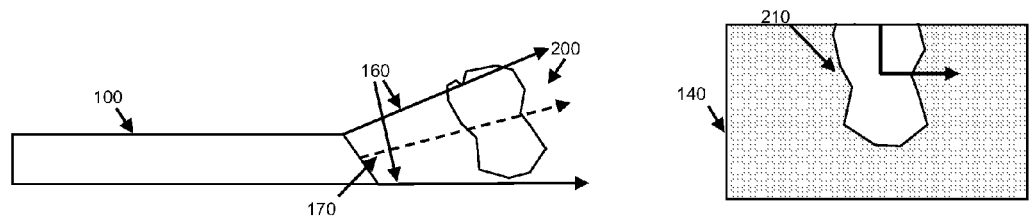

FIGS. 14*a* and 14*c* illustrate the endoscope (100), the object it is viewing (200) and the image seen by the endoscope camera (130) before the zoom. The solid arrows (160) show the limits of the FOV and the dashed arrow (170), the center of the field of view (FOV); since the object is in the center of the FOV, an image of the object (210) is in the center of the camera image (130). FIGS. 3B and 3D illustrate the endoscope (100), the object it is viewing (200) and the image seen by the endoscope camera (130) after the zoom. The solid arrows (160) show the limits of the FOV and the dashed arrow (170), the center of the field of view.

If the tip lens is set straight in the end of the endoscope (FIGS. 14*a* and 14*b*), an object (200) in the center of the field of view will be in the center of the field of view (FOV) (and the camera image) (130) both before (FIG. 14*a*) and after (FIG. 14*b*) the zoom. However, if the tip lens is set at an angle in the end of the endoscope (FIGS. 14*c* and 14*d*), then an object that is in the center of the FOV (and the camera image) before the zoom (FIG. 14*c*) will not be in the center of the FOV (or the camera image) after the zoom (FIG. 14*d*) since the direction of motion of the endoscope is not the direction in which the center of the field of view (170) points.

In an embodiment of the system of the present invention, unlike in conventional systems, the controlling means maintains the center of the field of view (FOV) during zoom independent of the tip lens angle. An advantage of controlling the zoom of the endoscope via a data processing system is that the tip lens angle does not need to be input to the data processing system, obviating a possible source of error.

According to one embodiment of the present invention, the endoscope's movement will be adjusted in order to maintain a constant field of view.

Example 15—Misalignment Rule/Function

According to another embodiment of the present invention, the system can inform the user of any misalignment of the same system.

Misalignment of the system may cause parasitic movement of the endoscope tip, where the endoscope tip does not move exactly in the expected direction. According to one embodiment of the system, the system comprises sensors (e.g., gyroscopes, accelerometers and any combination thereof) that calculate/estimates the position of the pivot point in real time in order to (a) inform the user of misalignment; or (b) calculate the misalignment so that the system can adjust its movement to prevent parasitic movement.

Example 16—Change of Speed Rule/Function

Figure 15:
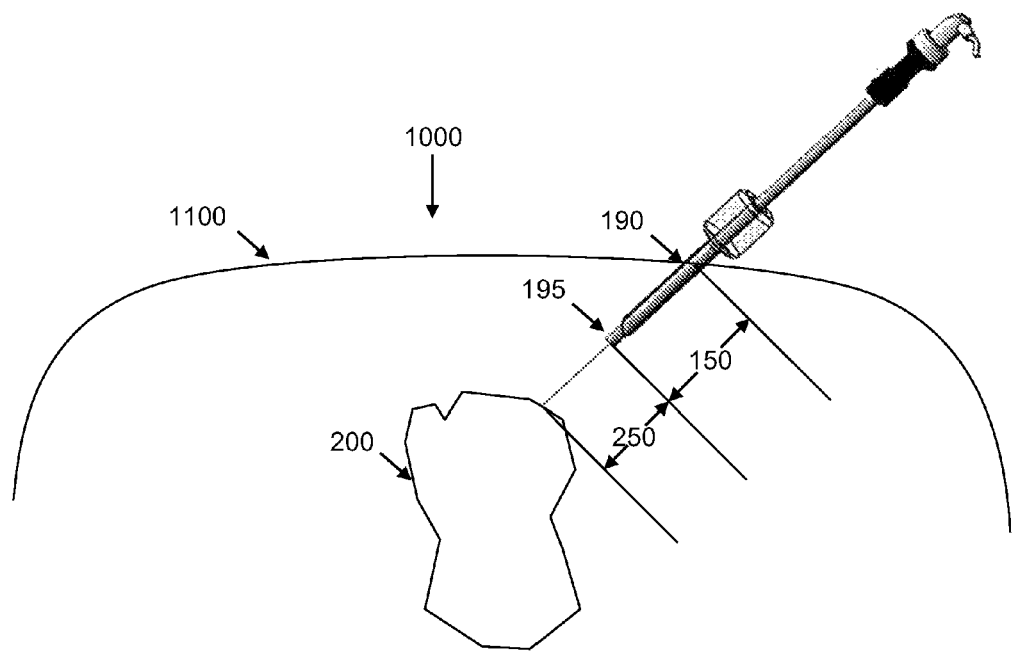
FIG. 15 schematically illustrates an embodiment of a tracking system with a change of speed rule/function.

In reference to FIG. 15, which shows, in a non-limiting manner, an embodiment of a tracking system with a change of speed rule/function.

In conventional endoscopic control systems, motion of the endoscope occurs at a single speed. This speed is fairly fast so that the endoscope can be moved rapidly between locations that are well separated. However, this means that making fine adjustments so difficult that fine adjustments are normally not made. In an embodiment of the present invention, the speed of the tip of the endoscope is automatically varied such that, the closer the endoscope tip is to an object, be it a tool, an obstacle, or the object of interest, the more slowly it moves. In this embodiment, as shown in FIG. 15, measurements are made of the distance X (150) from the tip (195) of the endoscope (100) to the pivot point of the endoscope (190), where said pivot point is at or near the surface of the skin (1100) of a patient (1000). Measurements are also made of the distance Y (250) from the tip of the endoscope (195) to the object in the center of the scene of view (200). From a predetermined velocity $V_p$, the actual velocity of the tip of the endoscope at a given time, $V_{act}$, is calculated from $$V_{act} \propto \frac{Y}{X} V_p$$

Therefore, the closer to the object at the center of the scene of view, the more slowly the endoscope moves, making it possible to use automatic control of even fine adjustments, and reducing the probability that the endoscope will come in contact with tissue or instruments.

According to one embodiment of the present invention, the velocity of the endoscope's movement will be adjusted as a function of the distance of the endoscope's tip from the organ\tissue.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A method of maneuvering an endoscope in a surgical procedure, comprising:
   mounting an endoscope to a robotic arm;
   positioning a distal end of the endoscope in a body cavity;
   capturing images of a surgical site in the body cavity using the endoscope and displaying the captured images on a touchscreen display;
   with the endoscope in a first position, receiving user input in response to a user touching a portion of the touchscreen display at which a region of interest in the surgical site is displayed, the portion offset from a center of the touchscreen display, said region of interest comprising a tissue region within the body cavity wherein receiving the user input includes receiving path input in response to a user tracing a pathway between a point at the center of the touch screen display and the region of interest on the displayed image; and in response to the user input, automatically repositioning the endoscope from the first position to a second position within the body cavity using the robotic arm, such that the region of interest is displayed in the center of the touchscreen display, wherein repositioning the endoscope includes causing the endoscope to move in the body cavity along a pathway within the body cavity corresponding to the pathway traced by the user on the displayed image.

2. The method of claim 1, wherein the method further includes:

in response to the user input, displaying a tag on the touchscreen display as an overlay over the region of interest.

3. The method of claim 1, wherein receiving the user input is in response to a user tapping a portion of the touchscreen display at which a region of interest in the surgical site is displayed.

4. A method of maneuvering an endoscope in a surgical procedure, comprising:

mounting an endoscope to a robotic arm;

positioning a distal end of the endoscope in a body cavity;

capturing images of a surgical site in the body cavity using the endoscope and displaying the captured images on a touchscreen display;

receiving user input in response to a user touching a portion of the touchscreen display at which a region of interest in the surgical site is displayed, said region of interest comprising a tissue region within the body cavity; and in response to the user input, repositioning the endoscope within the body cavity using the robotic arm, such that the region of interest is displayed in the center of the touchscreen display, wherein repositioning the endoscope comprises automatically determining a movement pathway for the endoscope within the body cavity, wherein receiving user input further includes receiving path input in response to a user tracing a pathway between a point at the center of the touch screen display and the region of interest on the displayed image, and repositioning the endoscope includes causing the endoscope to move in the body cavity along a pathway within the body cavity corresponding to the pathway traced by the user on the displayed image.

5. The method of claim 4, wherein receiving the user input is in response to a user tapping a portion of the touchscreen display at which a region of interest in the surgical site is displayed.

6. The method of claim 4, wherein the method further includes:

in response to the user input, displaying a tag on the touchscreen display as an overlay over the region of interest.

* * * * *